(12) United States Patent
Kunz et al.

(10) Patent No.: US 9,351,744 B2
(45) Date of Patent: *May 31, 2016

(54) PATIENT-SPECIFIC SURGICAL GUIDANCE TOOL AND METHOD OF USE

(71) Applicant: Queen's University at Kingston, Kingston (CA)

(72) Inventors: Manuela Kunz, Kingston (CA); John F. Rudan, Kingston (CA)

(73) Assignee: Queen's University at Kingston, Kingston, ON (CA)

( * ) Notice: Subject to any disclaimer, the term of this patent is extended or adjusted under 35 U.S.C. 154(b) by 184 days.

This patent is subject to a terminal disclaimer.

(21) Appl. No.: 13/893,484

(22) Filed: May 14, 2013

(65) Prior Publication Data

US 2014/0343403 A1   Nov. 20, 2014

Related U.S. Application Data

(63) Continuation of application No. 12/120,547, filed on May 14, 2008, now Pat. No. 8,444,651.

(60) Provisional application No. 60/917,713, filed on May 14, 2007.

(51) Int. Cl.
*A61B 17/17* (2006.01)
*A61B 17/16* (2006.01)
(Continued)

(52) U.S. Cl.
CPC ............ *A61B 17/175* (2013.01); *A61B 17/1604* (2013.01); *A61B 17/1739* (2013.01);
(Continued)

(58) Field of Classification Search
CPC ............. A61B 17/175; A61B 17/1757; A61B 17/1764; A61B 17/14; A61B 17/15; A61B 17/1604; A61B 17/148; A61B 2017/568; A61B 2017/1782; A61B 2019/461; A61B 2019/467
USPC .......................... 600/424, 426–429, 414–417; 606/87–89, 96–98, 130
See application file for complete search history.

(56) References Cited

U.S. PATENT DOCUMENTS

| 5,098,383 A | 3/1992 | Hemmy et al. |
| 5,250,050 A | 10/1993 | Poggie et al. |

(Continued)

FOREIGN PATENT DOCUMENTS

| EP | 1486900 A1 | 12/2004 |
| WO | WO93/25157 A1 | 12/1993 |

(Continued)

OTHER PUBLICATIONS

Botha, Technical Report: "DeVIDE—The Delft Visualisation and Image Processing Development Environment" TU Delft, The Netherlands, May 30, 2005, pp. i-49.

(Continued)

*Primary Examiner* — Long V Le
*Assistant Examiner* — Angela M Hoffa
(74) *Attorney, Agent, or Firm* — Stephen J. Scribner

(57) ABSTRACT

Presented is a preoperatively designed guidance tool for intraoperative use during bone or joint surgery wherein the guidance tool is specific to the anatomy of the patient being treated. The guidance tool comprises a body portion, a mating surface provided on the body portion for positioning the guidance tool on a corresponding registration surface of a patient's anatomy. The guidance tool further comprises at least one guide mechanism provided on the body portion for guiding a medical instrument at one or more preoperatively defined trajectories relative to a patient's anatomy. In the event of misalignment, the at least one guide mechanism is adjustable to alter the one or more preoperatively defined trajectories if necessary during intraoperative use. Also presented is a preoperative process for designing the guidance tool.

17 Claims, 24 Drawing Sheets

(51) Int. Cl.
  *A61B 17/14* (2006.01)
  *A61B 17/15* (2006.01)
  *A61B 17/56* (2006.01)
  *A61B 19/00* (2006.01)

(52) U.S. Cl.
  CPC ............ *A61B17/1757* (2013.01); *A61B 17/14* (2013.01); *A61B 17/148* (2013.01); *A61B 17/15* (2013.01); *A61B 17/1764* (2013.01); *A61B 2017/1778* (2013.01); *A61B 2017/1782* (2013.01); *A61B 2017/568* (2013.01); *A61B 2019/461* (2013.01); *A61B 2019/467* (2013.01)

(56) References Cited

U.S. PATENT DOCUMENTS

| | | | |
|---|---|---|---|
| 5,682,886 A | 11/1997 | Delp et al. | |
| 5,768,134 A | 6/1998 | Swaelens et al. | |
| 5,871,018 A | 2/1999 | Delp et al. | |
| 5,910,143 A | 6/1999 | Cripe et al. | |
| 5,967,777 A | 10/1999 | Klein et al. | |
| 6,117,143 A | 9/2000 | Hynes et al. | |
| 6,259,943 B1 * | 7/2001 | Cosman et al. | 600/429 |
| 6,282,437 B1 * | 8/2001 | Franck et al. | 600/429 |
| 6,298,262 B1 | 10/2001 | Franck et al. | |
| 6,327,491 B1 | 12/2001 | Franklin et al. | |
| 6,351,662 B1 * | 2/2002 | Franck et al. | 600/429 |
| 6,529,765 B1 * | 3/2003 | Franck et al. | 600/427 |
| 6,546,277 B1 * | 4/2003 | Franck et al. | 600/426 |
| 6,645,214 B2 * | 11/2003 | Brown et al. | 606/102 |
| 6,738,657 B1 | 5/2004 | Franklin et al. | |
| 6,944,518 B2 | 9/2005 | Roose | |
| 7,651,506 B2 | 1/2010 | Bova et al. | |
| 7,962,196 B2 * | 6/2011 | Tuma | 600/424 |
| 8,043,297 B2 | 10/2011 | Grady et al. | |
| 8,092,465 B2 | 1/2012 | Metzger et al. | |
| 8,444,651 B2 | 5/2013 | Kunz et al. | |
| 2004/0092932 A1 | 5/2004 | Aubin et al. | |
| 2005/0148843 A1 | 7/2005 | Roose | |
| 2005/0170311 A1 | 8/2005 | Tardieu et al. | |
| 2006/0094951 A1 | 5/2006 | Dean et al. | |
| 2006/0212044 A1 | 9/2006 | Bova et al. | |
| 2007/0239166 A1 * | 10/2007 | McGuire et al. | 606/86 |
| 2008/0287954 A1 * | 11/2008 | Kunz et al. | 606/87 |
| 2012/0245647 A1 * | 9/2012 | Kunz et al. | 606/86 R |

FOREIGN PATENT DOCUMENTS

| | | |
|---|---|---|
| WO | WO96/36284 A1 | 11/1996 |
| WO | WO99/26540 A1 | 6/1999 |
| WO | WO99/32045 A1 | 7/1999 |
| WO | WO01/77988 A2 | 3/2004 |
| WO | WO2004/017843 A1 | 3/2004 |
| WO | WO2005/110250 A1 | 3/2004 |
| WO | WO2006/060795 A1 | 6/2006 |
| WO | WO2007/097854 A2 | 8/2007 |

OTHER PUBLICATIONS

Rademacher et al., "Computer Assisted Orthopaedic Surgery by Means of Individual Templates Aspects and Analysis of Potential Application", MRCAS, 42-48 (1994).

Rademacher et al., "Computer Assisted Orthopaedic Surgery with Image Based Individual Templates", Clinical Orthopaedics and Related Research, 354, 28-38, (1998).

A pamphlet entitled "DePuy Preservation Design Rationale and Surgical Technique", DePuy Orthopaedics, Inc. 2006 (Rev. 3) 1-30.

Extended European Search Report dated Jan. 24, 2013 for counterpart European Patent Application No. 08747319.4.

International Search Report and Written Opinion for International Application No. PCT/CA2008/000930 filed May 14, 2008.

International Preliminary Report on Patentability for International Application No. PCT/CA2008/000930 filed May 14, 2008.

* cited by examiner

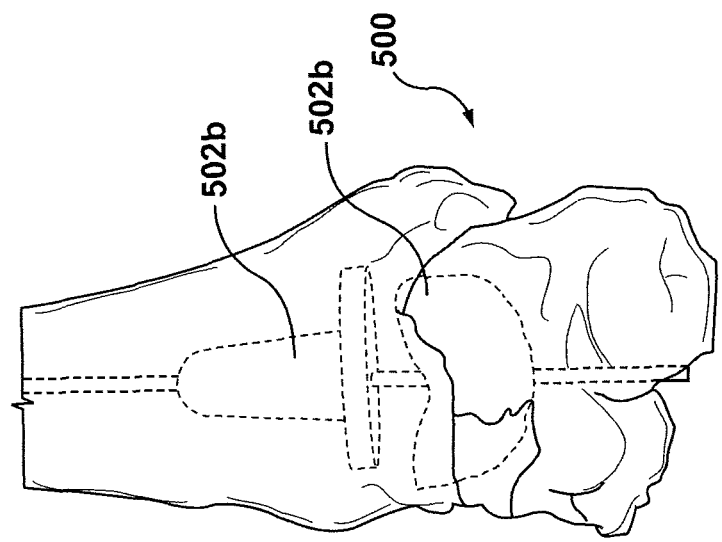
FIG. 18b
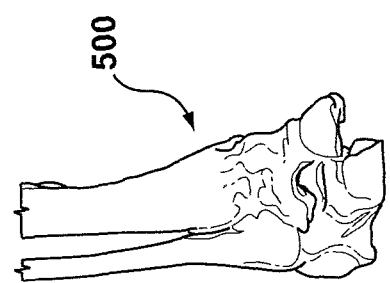
FIG. 18a
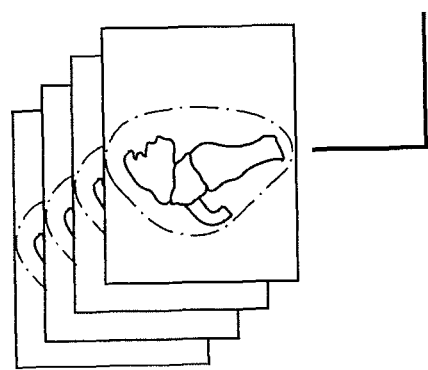

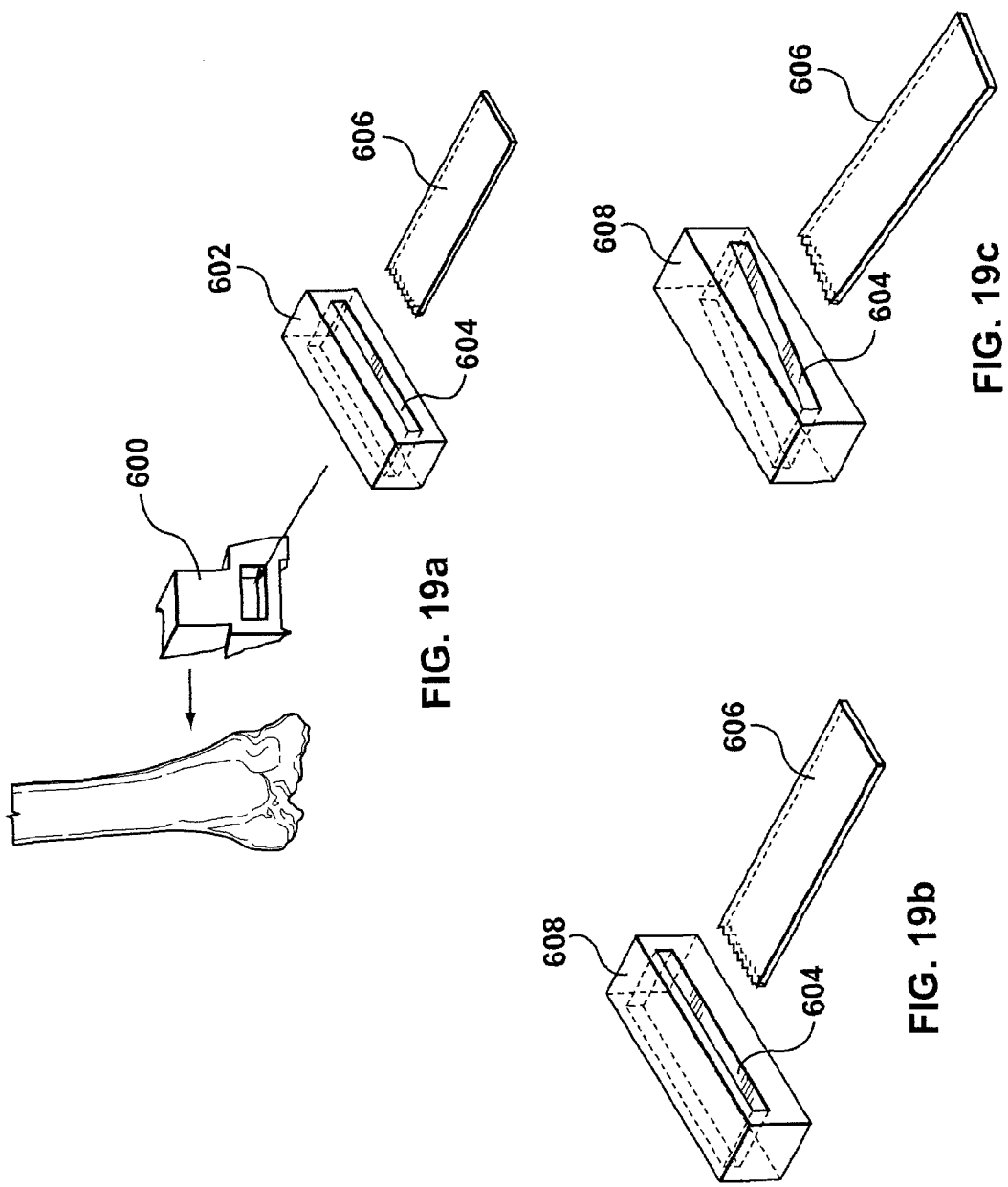

PATIENT-SPECIFIC SURGICAL GUIDANCE TOOL AND METHOD OF USE

RELATED APPLICATIONS

This application is a continuation of U.S. patent application Ser. No. 12/120,547, filed on May 14, 2008, now U.S. Pat. No. 8,444,651, issued on May 21, 2013, and claims the benefit of U.S. Provisional Patent Application No. 60/917,713 filed on May 14, 2007, the contents of which are incorporated herein by reference.

FIELD

The present invention pertains to a patient-specific alignment and guidance tool for a surgical procedure, and software associated with designing such a tool. The present invention also pertains to a pre-operative process using the software for designing the patient-specific alignment and guidance tool. The present invention also pertains to an intraoperative process wherein the patient-specific alignment and guidance tool is used during a surgical procedure.

BACKGROUND

Bone and joint surgical procedures are well known in the art. To improve on conventional surgical techniques, imaging technologies and computers are increasingly being adopted and implemented by surgeons. The primary drive in developing such technology is to reduce the overall invasiveness of the procedure, while maintaining or increasing the overall accuracy.

Computer assisted surgery (CAS) is now quite common for a range of surgical procedures. Surgeons are able to use computer tracking technology to visually map a patient's anatomy both before and during the surgical procedure. CAS also provides increased precision in targeting a particular site for correction. These techniques are also very useful for determining the optimal size and location of prosthetic implants.

Publications in the area of CAS have shown increased accuracy and/or precision during the intraoperative procedure; however, these systems add not only higher costs to the surgery, but also increased surgical time. The necessary technical equipment related to conventional computer-assisted systems makes additional surgeon and operating room (OR) team training necessary. Additionally, not all hospitals have access to CAS techniques. Furthermore, the accuracy benefits of CAS are not necessarily reflected in the patient outcomes, as there is significant variability amongst surgeons in their ability to perform precise surgical operations.

Also known in the art is the use of templates for surgical procedures. Templates may be prepared using medical imaging techniques and they can enhance the accuracy of the procedure in the operating room. However, a drawback of such templates is that the alignment provided cannot be verified or adjusted intraoperatively.

In view of the foregoing disadvantages, it would be beneficial to implement a procedure that combines the accuracy benefits of CAS with the precision, repeatability, low cost and ease of use benefits associated with surgical alignment tools.

SUMMARY

According to one aspect, provided is a guidance tool for intraoperative use during bone or joint surgery wherein said guidance tool is specific to the anatomy of the patient being treated, said guidance tool comprising a guide component for guiding a medical instrument at one or more predetermined trajectories relative to a patient's anatomy, and a registration component attached to said guide component for positioning said guidance tool on a patient's anatomy, wherein said guide component can be adjusted to alter the one or more predetermined trajectories if necessary during intraoperative use.

In one embodiment, the guidance tool further comprises a verification component for mechanically verifying correct position of the guidance tool on the patient's anatomy.

According to a further aspect, provided is a preoperative process for designing a guidance tool for intraoperative use during bone or joint surgery wherein said guidance tool is specific to the anatomy of the patient being treated, said process comprising creating a 3-D surface model of the patient's anatomy, using the 3-D surface model of the patient's anatomy to preoperatively determine a trajectory for pin placement, designing a virtual guidance tool for registering against the patient's anatomy, said virtual guidance tool providing a guide component for guiding pin placement at the predetermined trajectory relative to the patient's anatomy, and a registration component attached to said guide component for positioning said guidance tool on the patient's anatomy, preoperatively assessing the fit, size and/or design of the guidance tool on the patient anatomy using the 3-D surface model of the patient's anatomy, and adjusting the design of the guidance tool as necessary to achieve a correct fit.

According to another aspect, provided is a method of facilitating bone or joint surgery using a preoperatively designed patient-specific guidance tool, said method comprising the steps of placing the guidance tool directly upon the patient's anatomy for which it has been designed, said guidance tool providing a guide component establishing a predetermined trajectory for pin placement, assessing the predetermined trajectory governed by the guide component of the guidance tool, determining whether adjustments to the guide component are necessary for achieving an optimal placement of said pin, and adjusting, if necessary, the guide component of said guidance tool to achieve an alternate trajectory for optimal placement of said pin.

According to a further aspect, provided is a method of verifying correct placement of a preoperatively designed patient-specific guidance tool, comprising intraoperatively placing the guidance tool directly upon the patient's anatomy for which it has been designed, the guidance tool having a guide component establishing a predetermined trajectory for pin placement and a verification component for mechanically verifying correct position of the guidance tool on the patient's anatomy, and using the verification component to mechanically verify correct position of the guidance tool on the patient's anatomy.

According to an aspect, provided is a preoperatively designed guidance tool for intraoperative use during bone or joint surgery wherein said guidance tool is specific to the anatomy of the patient being treated, said guidance tool comprising:

a body portion;

a mating surface provided on said body portion, said mating surface for positioning said guidance tool on a corresponding registration surface of a patient's anatomy; and at least one guide mechanism provided on said body portion, said at least one guide mechanism for guiding at least one medical instrument at one or more preoperatively defined trajectories relative to a patient's anatomy;

wherein said at least one guide mechanism is adjustable to alter the one or more preoperatively defined trajectories if necessary during intraoperative use.

In some embodiments, said body portion comprises a guide component, and a registration component, each of said at least one guide mechanism and said mating surface being provided on at least one of said guide component and said registration component.

In some embodiments, said body portion further comprises a stability component.

In some embodiments, said mating surface on said body portion is discontinuous having regard to the patient's anatomy.

In some embodiments, said mating surface comprises a profile that is complementary to characteristic anatomical landmarks found on said registration surface of a patient's anatomy.

In some embodiments, the guide tool further comprises a removable verification tool for mechanically verifying the correct position of the guidance tool on the patient's anatomy, having regard to preoperatively selected anatomical landmarks.

In some embodiments, said verification tool is configured for insertion into said guide mechanism.

In some embodiments, said verification tool comprises at least one graduated section to determine misalignment of the guidance tool relative to said one or more preoperatively defined trajectories.

In some embodiments, said verification tool comprises two graduated section for providing misalignment values relative to the patient's anatomy, a first graduated section providing misalignment values in a longitudinal direction, and a second graduated section providing misalignment values in a radial direction.

In some embodiments, said at least one graduated section is a sliding ruler is provided with graduations for measuring said misalignment.

In some embodiments, the guidance tool further comprises locking keys provided on said body portion for aligning said verification tool in a preoperatively defined position for comparison with previously selected anatomical landmarks.

In some embodiments, said guide mechanism comprises a guide channel and corresponding instrument sleeve for placement within said guide channel, said instrument sleeve for guiding said medical instrument at said one or more preoperatively defined trajectories relative to a patient's anatomy.

In some embodiments, said guide mechanism comprises a realignment sleeve for use in place of said instrument sleeve, said realignment sleeve providing a realignment of the instrument trajectory where the established trajectory requires adjustment.

In some embodiments, said realignment sleeve is configured with a translational offset relative to the central axis of the sleeve.

In some embodiments, said realignment sleeve is configured with an angled offset relative to the central axis of the sleeve.

In some embodiments, said realignment sleeve is configured with a combined translational offset and angled offset relative to the central axis of the sleeve.

In some embodiments, the translational offsets are from about 0 to about 5 mm from the central axis.

In some embodiments, the translational offsets are provided in increments ranging from about 0.01 mm to about 1 mm.

In some embodiments, the angled offset is from about 0 to about 5° relative to the central axis.

In some embodiments, the angled offsets are provided in increments ranging from about 0.05° to about 1°.

According to another aspect, provided is a preoperative process for designing at least one guidance tool for intraoperative use during bone or joint surgery wherein said at least one guidance tool is specific to the anatomy of the patient being treated, said process comprising creating a 3-D surface model of the patient's anatomy;

using the 3-D surface model of the patient's anatomy to preoperatively determine a trajectory of at least one medical instrument during bone or joint manipulation;

designing at least one guidance tool for registering against the patient's anatomy, said at least one guidance tool providing a guide mechanism and a mating surface, said guide mechanism for guiding said at least one medical instrument during said bone or joint manipulation at the preoperatively defined trajectory relative to a patient's anatomy, said mating surface providing positional registration of said at least one guidance tool on the patient's anatomy; and preoperatively assessing the fit, size and design of the at least one guidance tool on the patient anatomy using the 3-D surface model of the patient's anatomy, and adjusting the design of the at least one guidance tool as necessary to achieve a correct fit.

In some embodiments, said 3-D surface model of the patient's anatomy is created by one or more of CT, MRI, X-ray, and ultrasound.

In some embodiments, said assessment of fit involves a quantitative figure of merit determination based on an examination of characteristic landmarks on said mating surface relative to said patient's anatomy.

In some embodiments, the preoperative process further comprises the identification of at least one characteristic anatomical landmark to be used in connection with a removable verification tool for mechanically verifying correct position of the at least one guidance tool on the patient's anatomy, said verification tool being configured for attachment to the at least one guidance tool.

In some embodiments, multiple guidance tools are designed for intraoperative use for a particular procedure.

According to a further aspect, provided is a method of facilitating bone or joint surgery using a preoperatively designed patient-specific guidance tool, said method comprising the steps of:

placing the guidance tool directly upon the patient's anatomy for which it has been designed, said guidance tool providing a mating surface and a guide mechanism, said guide mechanism for guiding at least one medical instrument during bone or joint manipulation at a preoperatively defined trajectory relative to a patient's anatomy, said mating surface providing positional registration of said guidance tool on said patient's anatomy;

assessing the position of the guidance tool upon the patient's anatomy;

assessing the preoperatively defined trajectory governed by the guide mechanism of the guidance tool;

determining whether adjustments to the guide mechanism are necessary for achieving an optimal trajectory of said at least one medical instrument; and adjusting, if necessary, the guide mechanism of said guidance tool to achieve an alternate trajectory for said at least one medical instrument.

In some embodiments, a verification tool, fitted to said guide mechanism of the guidance tool, is used to assess the position and orientation of the guidance tool having regard to the preoperatively defined trajectory.

In some embodiments, said verification tool comprises at least one graduated section to determine misalignment of the guidance tool relative to said one or more preoperatively defined trajectories.

In some embodiments, said verification tool comprises two graduated sections for providing misalignment values relative to the patient's anatomy, a graduated section providing misalignment values in a longitudinal direction, and a second graduated section providing misalignment values in a radial direction.

In some embodiments, said at least one graduated section is a sliding ruler provided with graduations for measuring said misalignment.

In some embodiments, said guide mechanism comprises a guide channel and an instrument sleeve, and wherein a correction to realign said trajectory is provided by a realignment instrument sleeve used in place of said instrument sleeve to achieve the corrected trajectory.

In some embodiments, said guidance tool is retained in place on the patient's anatomy manually by hand.

In some embodiments, said guidance tool is retained in place on the patient's anatomy using suitable fasteners selected from the group consisting of pins, screws, straps, clamps, zip-ties and elastic fasteners.

In some embodiments, said verification tool is further used to visualize and assess the preoperatively defined trajectory governed by the guide mechanism, wherein said verification tool is rotatable relative to said guidance tool.

According to a still further aspect, provided is a method of realigning a trajectory in a preoperatively designed patient-specific guidance tool, comprising:

intraoperatively placing the guidance tool directly upon the patient's anatomy for which it has been designed, the guidance tool having a guide mechanism establishing a preoperatively defined trajectory for at least one medical instrument and a verification tool for mechanically verifying correct position of the guidance tool on the patient's anatomy; and using the verification tool to mechanically verify correct position of the guidance tool on the patient's anatomy.

In some embodiments, upon detection of a misalignment, said verification tool is used to quantify the misalignment using at least one graduated section provided on said verification tool.

In some embodiments, upon detection of a misalignment, said verification tool is used to quantify the misalignment using at least two graduated sections provided on said verification tool.

In some embodiments, at least one of a reference chart, table or realignment calculator is used to determine a correct realignment trajectory based on the registered misalignment, so as to return to the preoperatively defined trajectory.

In some embodiments, said reference chart and/or table are preoperatively generated based on preoperative planning having regard to the geometry of the guidance tool and the patient's specific anatomy.

In some embodiments, said guide mechanism is adjusted to accord with the calculated realignment trajectory.

According to yet another aspect, provided is a method of verifying correct placement of a preoperatively designed patient-specific guidance tool, comprising:

intraoperatively placing the guidance tool directly upon the patient's anatomy for which it has been designed, the guidance tool having a guide mechanism establishing a preoperatively defined trajectory for at least one medical instrument and a verification tool for mechanically verifying correct position of the guidance tool on the patient's anatomy; and using the verification tool to mechanically verify correct position of the guidance tool on the patient's anatomy.

BRIEF DESCRIPTION OF THE DRAWINGS

Embodiments will now be described, by way of example only, with reference to the attached Figures, wherein:

FIGS. 7a to 7c are perspective views of the femur with the guidance tool in position, wherein FIGS. 7b and 7c show a verification tool used to verify correct positioning of the guidance tool on the femur;

FIGS. 18a through 18d are illustrations of how a guidance tool can similarly be used in total ankle arthroplasty;

FIGS. 19a through 19c show an alternate guidance tool for total ankle arthroplasty.

DESCRIPTION OF ILLUSTRATIVE EMBODIMENTS

Figure 1:
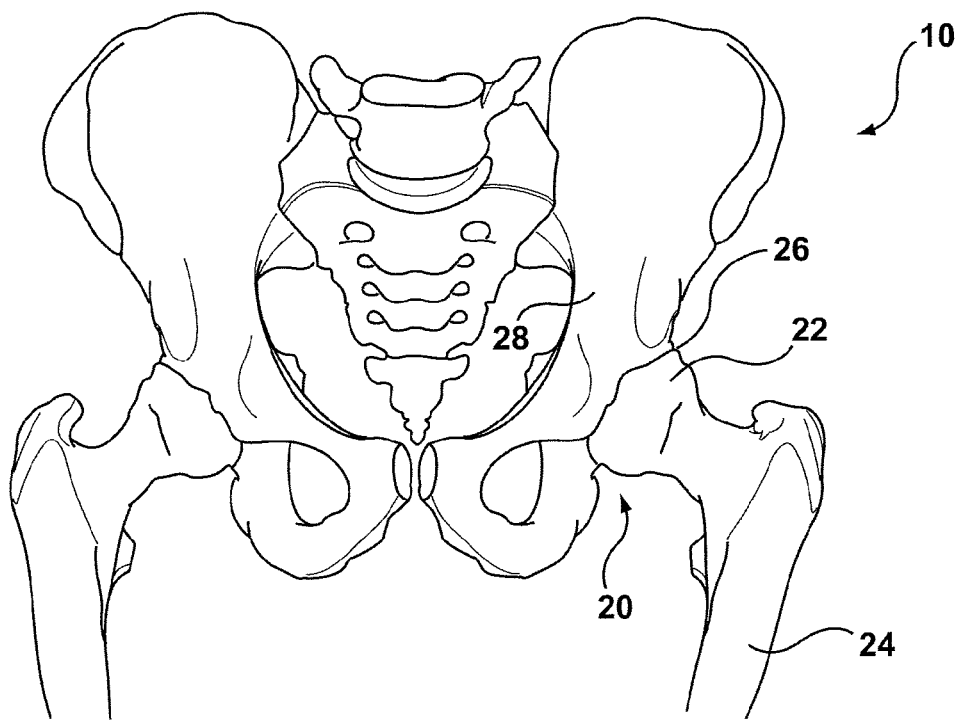
FIG. 1 is a skeletal representation of a human hip joint.

The following discussion presents an embodiment wherein the patient specific guidance tool and associated methodology/procedure for construction and implementation are presented largely within the framework of hip resurfacing. One will appreciate, however that the guidance tool and associated methodology/procedure may be implemented in a range of bone and joint surgical applications. For example, the following discussion may find application for use in, but not limited to, ankle, knee and shoulder surgery, spine fusion, craniomaxillofacial surgery, osteotomies, fracture treatment and fixation, scoliosis, wrist surgery, and mosaicplasty. Thus, the following description is intended as an exemplification of illustrative embodiments, and is not intended to limit the description to the particular embodiments illustrated.

Unlike prior art technologies that incorporate intraoperative computer-assisted methods for pin-drilling guidance, the embodiment discussed below provides an individualized, patient-specific procedure that begins prior to surgery. The method generally initiates with a pre-operative planning stage in which a virtual 3-dimensional (3-D) iso-surface model of the patient's specific anatomy is created. Specifically, the anatomy of the patient undergoes preoperative medical imaging by one or more of computed tomography (CT), magnetic resonance imaging (MRI), ultrasound, X-ray, etc. With this data, a 3-D computer iso-surface model representing bone and/or soft tissue of the patient's anatomy is produced, upon which the location and/or trajectory for drilling, cutting, reaming, resurfacing, and/or modifying of bone and/or other tissue, for a central pin, guide pin or other surgical implement, can be preoperatively determined. The specific patient anatomy and the preoperatively determined trajectories are then factored into the manufacture of a patient-specific guidance tool to assist intraoperatively. The preoperative design phase preferably includes a virtual assessment of quality of fit, and further enables the design and manufacture of a verification tool to verify position/orientation of the guidance tool relative to the preoperatively determined trajectory and the patient's anatomy.

As mentioned above, the patient-specific guidance tool and associated methodology/procedure for construction and implementation (generally termed "patient-specific procedure") is herein initially discussed within the framework of hip resurfacing. Hip resurfacing is a relatively new procedure that is seen as an attractive alternative to total hip replacement (THR) for younger, more active patients. In hip resurfacing the femoral head is not replaced, as is done in THR, but instead a femoral component is implanted on the femoral head. The femoral component includes a metallic hemisphere that effectively replaces the articular cartilage covering the femoral head, and forms the bearing surface of the femoral component, and one of the articulating surfaces of the hip joint. The femoral component also includes a central pin that is inserted into the femoral head/neck, which maintains the correct position of the femoral component. The hemisphere subsequently mates with an acetabular component that is positioned in and provides a lining in the acetabulum of the pelvic bone, and provides the other articulating surface of the hip joint.

The most common cause of early failure of a hip resurfacing procedure is femoral neck fracture. While careful patient selection can reduce the risk of neck fractures, a further significant contributing factor is the orientation of the hemispherical femoral component. A non-optimal orientation of the femoral component can result in notching of femoral neck cortex, which increases the risk of fracture. Also, excessive tilting of the femoral component in varus may result in greater stresses within the bone, which adds to the risk of neck fractures. The size of the component may also play an important role in early clinical success. The appropriate size of the femoral component should be large enough to prevent impingement, but small enough to avoid large bone resection of the acetabulum.

Referring now to FIG. 1, a skeletal representation of a hip is indicated generally at reference numeral 10. The hip joint 20 is a synovial joint comprised of the rounded head 22 of the femur 24 and the cup-like acetabulum 26 of the pelvis 28; the primary function of this joint being to support the weight of the body in both static and dynamic postures.

Figure 2:
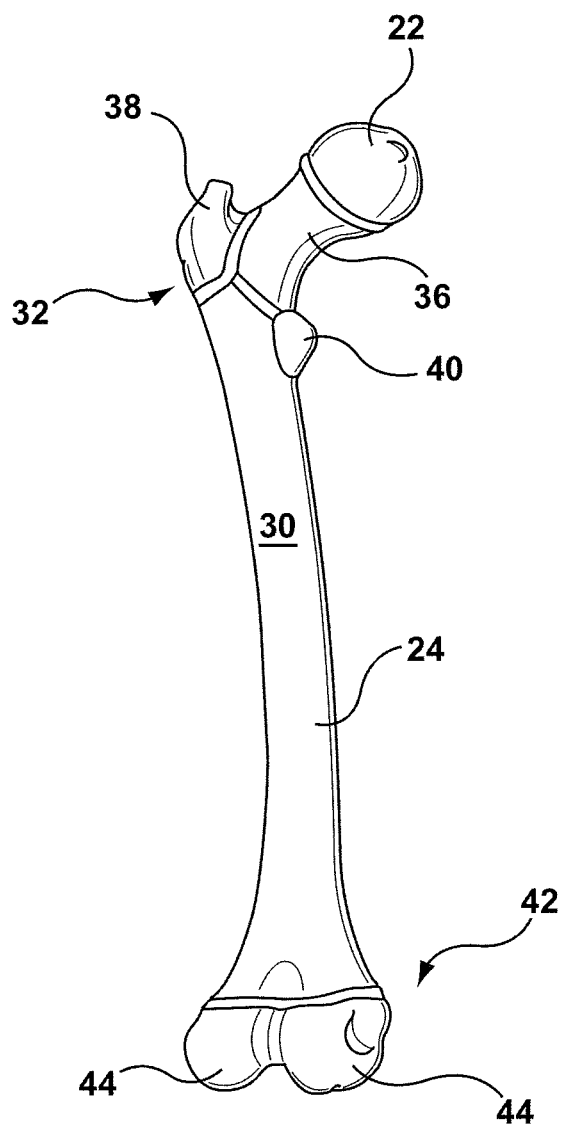
FIG. 2 is a skeletal representation of a human femur.

The femur 24 is shown in greater detail in FIG. 2. As shown, the femur 24 is divisible into a body 30, and two extremities. The upper extremity 32 comprises the head 22, a neck 36, a greater trochanter 38 and a lesser trochanter 40; while the lower extremity 42 largely comprises a medial condyle 44 and a lateral condyle 46. Between the two extremities is the body 30 (or shaft) which is generally cylindrical in form.

Figure 3:
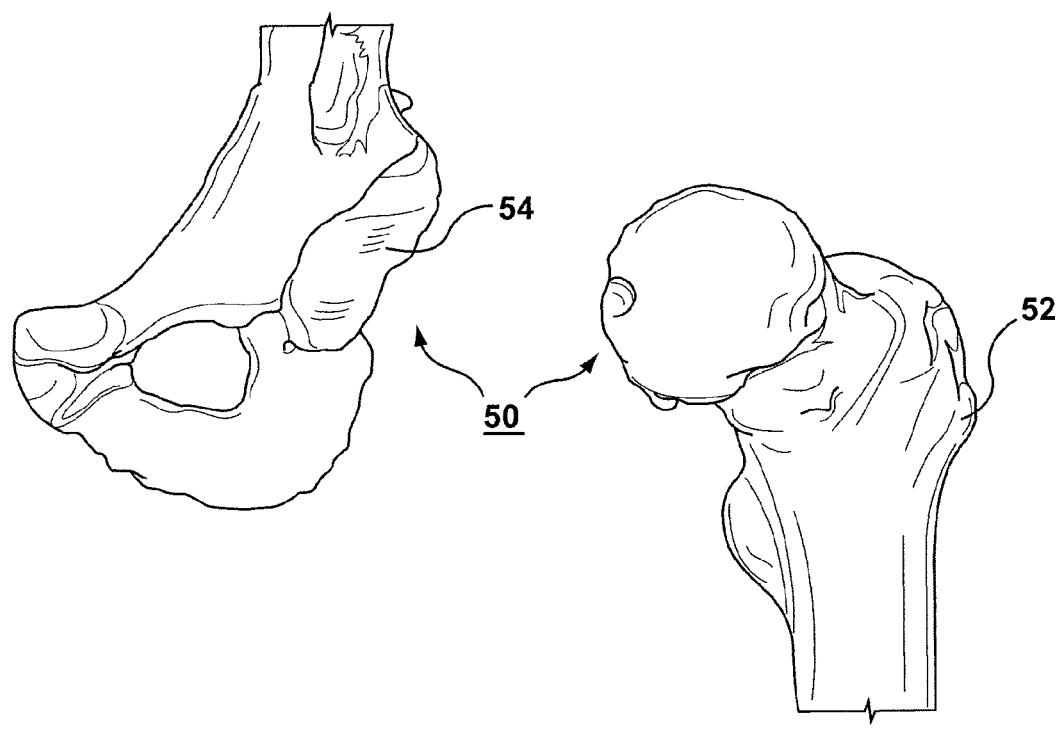
FIG. 3 is a 3-D computer iso-surface model representing bone and/or soft tissue of the proximal femur and acetabulum.

Referring now to FIG. 3, hip resurfacing carried out in accordance with the herein described patient-specific procedure begins with a pre-operative planning stage in which the 3-D iso-surface model of the patient's specific hip joint anatomy is created. As shown, the 3-D iso-surface model 50 represents to a high degree of accuracy the bone and/or soft tissue of the patient's anatomy. Shown in FIG. 3 is a virtual representation of the proximal femur 52 and the acetabulum 54.

Using the virtual 3-D iso-surface model 50, the drilling trajectory for a central pin or guide pin is preoperatively determined. As the central pin will form the reference or guide for all subsequent procedures, it is desirable to establish and achieve a precise central pin trajectory. To determine the trajectory, a Virtual Surgical System (VSS) software package is used, developed by iGo Technologies Inc. (Kingston, Canada). One will appreciate, however, that other virtual surgical planning programs are applicable and may be substituted.

Figure 4A:
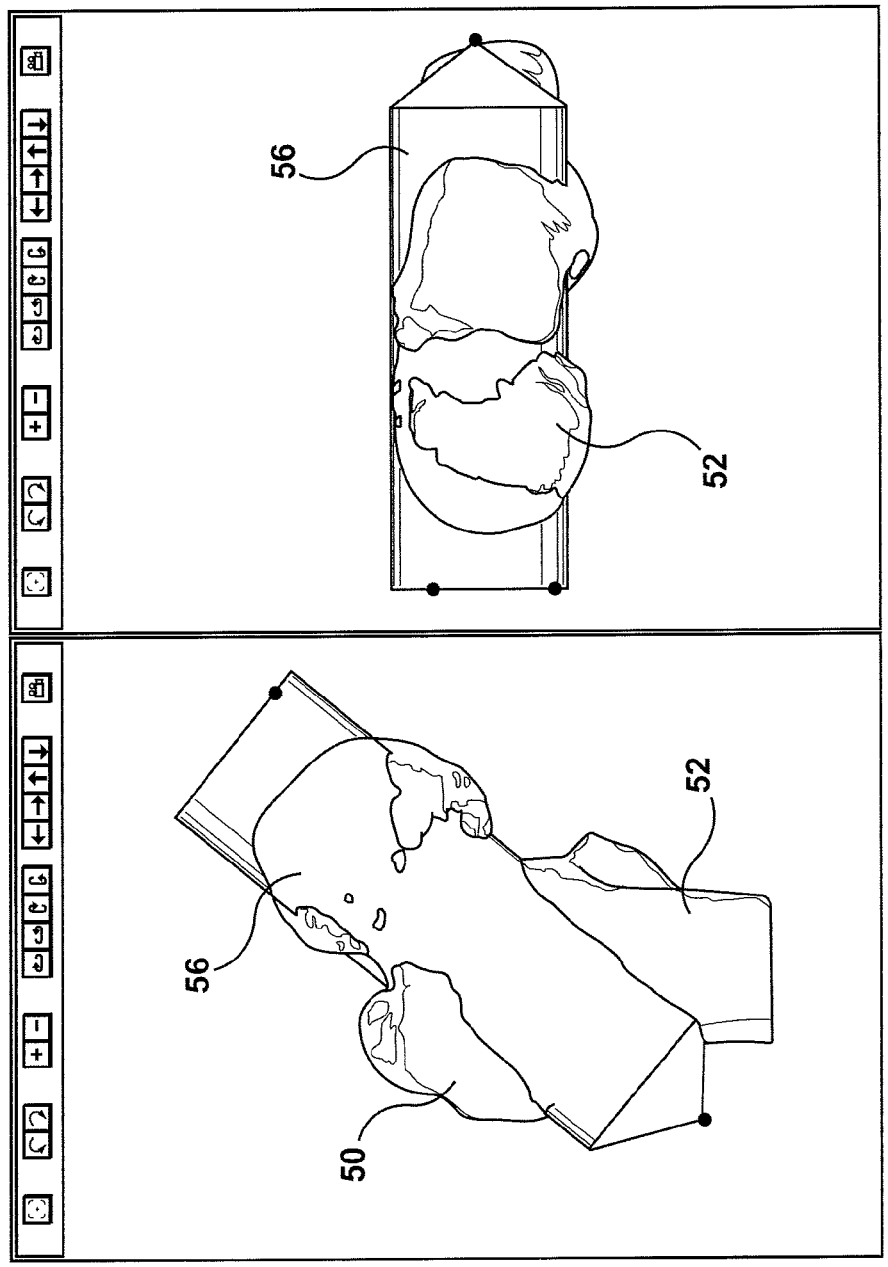
FIGS. 4a and 4b show the establishment of a drilling trajectory for the central pin.
Figure 4B:
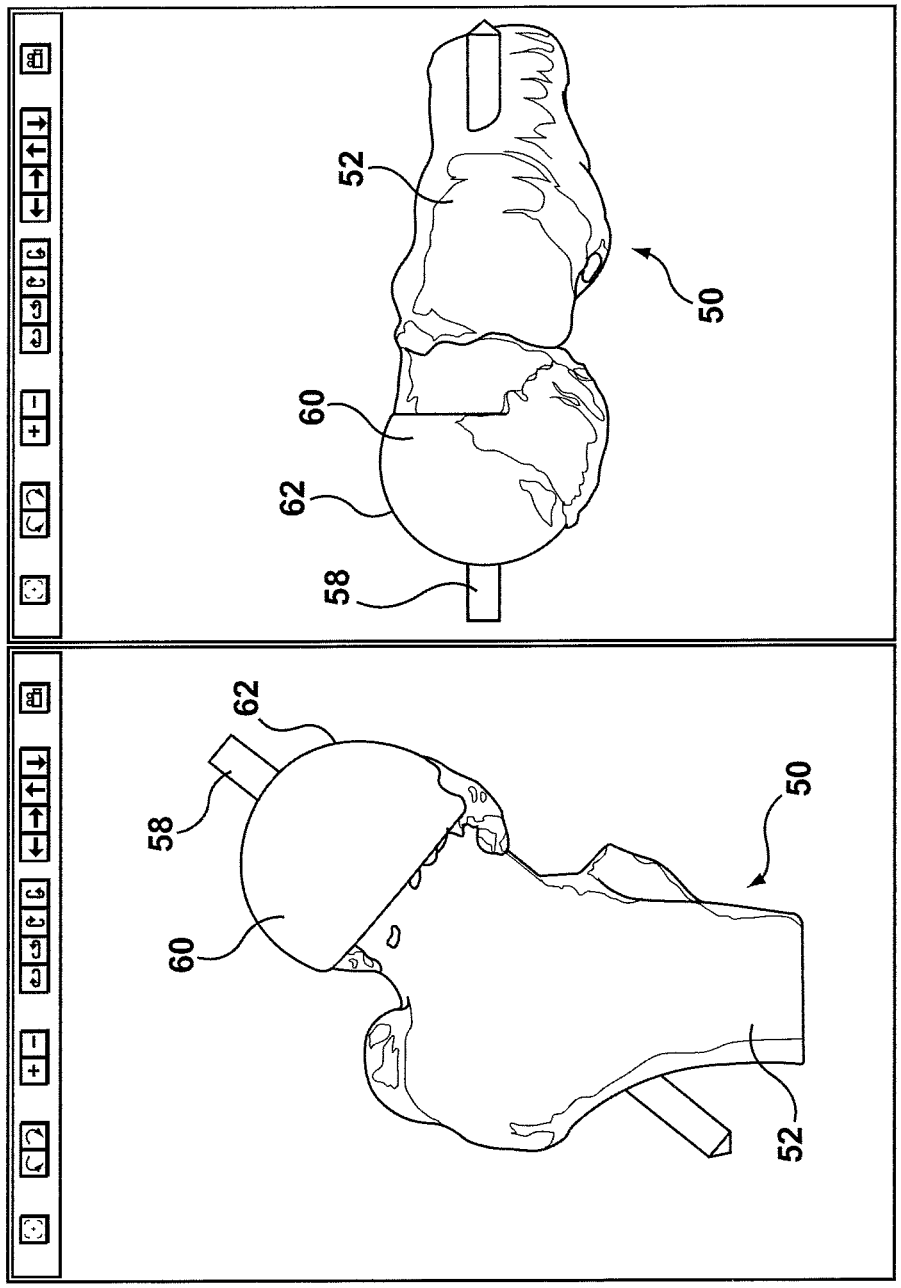
Figure 5:
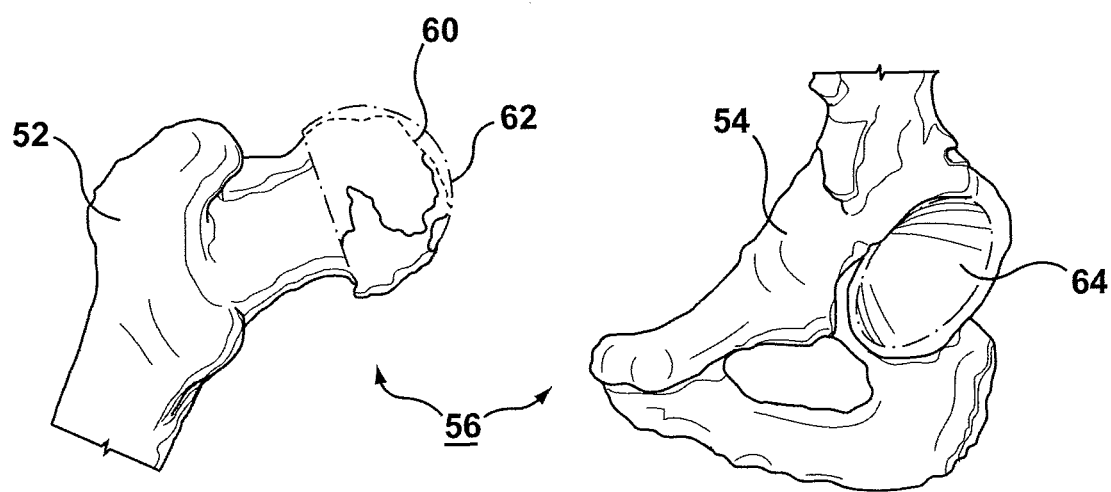
FIG. 5 is a 3-D computer iso-surface model representing bone and/or soft tissue of the proximal femur and acetabulum, wherein the virtual femoral and acetabular components are fitted to the virtual model.

As shown in FIG. 4a, using the VSS software and the established 3-D iso-surface model 50 of the proximal femur 52, the anatomical position/orientation of the neck-shaft axis 56 relative to the femur 52 is registered. With this alignment information, the position and orientation of the trajectory 58 for the central pin is established. The femoral component 60, which comprises an articulating or bearing surface 62 and the central pin is then fitted to the femur 52 in the virtual space, as shown in FIGS. 4b and 5. In addition, and quite advantageously, having regard to the alignment information, the established trajectory 58 and the established positioning/orientation of the femoral component, the hip joint can be assessed for possible intraoperative complications, such as notching of the femoral neck cortex during reaming of the femoral head. Based on these assessments, alterations to the positioning/orientation of the femoral component can more safely and accurately be made preoperatively.

With the drilling trajectory 58 determined, the 3-D iso-surface model 50 is then used to establish an accurate sizing of the femoral and acetabular components, so as to ensure that the femoral component does not infringe the femoral neck, and that excessive resection of the acetabulum is not required. As shown in FIG. 5, the 3-D iso-surface model 50 serves as a pre-operative virtual space to fit the femoral component 60 and the acetabular component 64 to the individual patient-specific anatomy.

Figure 6:
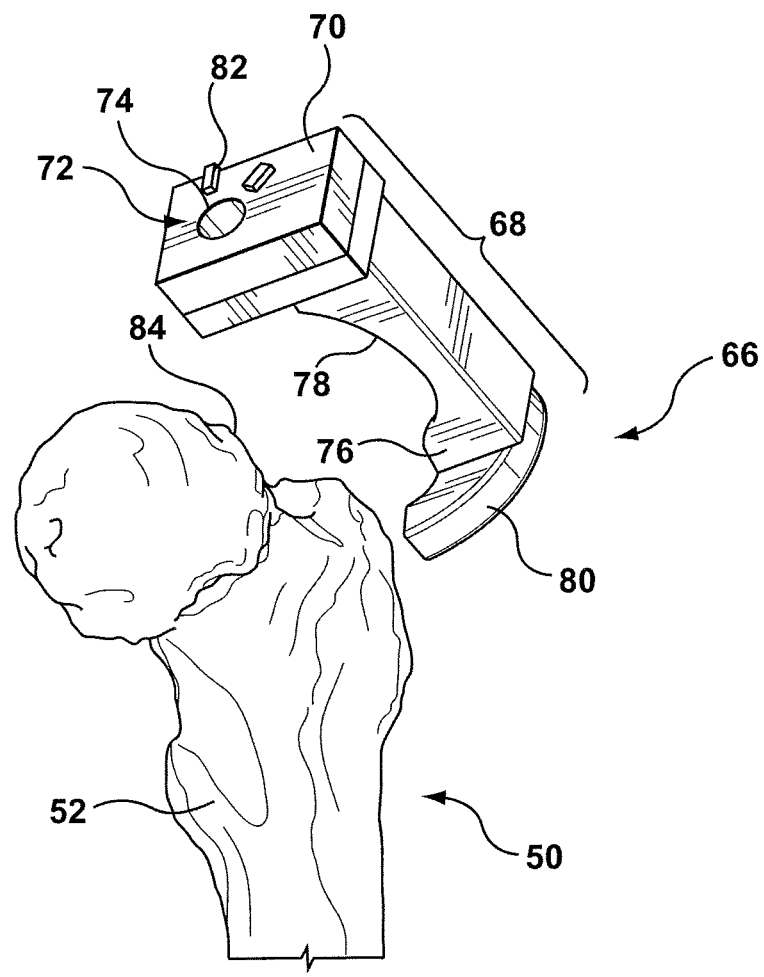
FIG. 6 is a 3-D computer iso-surface model representing bone and/or soft tissue of the proximal femur, wherein the guidance tool is fitted to the virtual model.

Continuing with the preoperative planning stage, the 3-D iso-surface model and the established drilling trajectory information are used to design a patient-specific guidance tool 66 for accurately achieving the planned drilling trajectory for the central pin of the femoral component. A virtual representation of the patient-specific guidance tool 66 relative to the patient-specific 3-D iso-surface model 50 is shown in FIG. 6. In general, the guidance tool comprises at least one guide component that serves as a drill guide, at least one registration component for providing a mating surface relative to the patient's anatomy, and optionally, at least one stability component for adding stability to the tool when placed upon the patient's anatomy.

As used herein, the term "mating surface" refers to a 3-D surface which is complementary to and mates with the 3-D surface (registration surface) of a selected portion of a patient's anatomy. A guidance tool as described herein includes at least one mating surface.

As used herein, the term "registration surface" refers to the 3-D surface of a selected portion of a patient's anatomy.

In the embodiment shown in FIG. 6, the guidance tool 66 comprises a body portion 68 that is placed directly upon the patient's anatomy. Although the body portion 68 of the guidance tool 66 can assume a wide range of configurations, depending on the implementation, the body portion 68 as shown in FIG. 6 can be described by way of three components. First, provided is a guide component 70 for establishing the planned central pin trajectory 58. The guide component 70 is provided with a guide mechanism 72 comprising a guide channel 74 for later receipt of a removable drill sleeve following correct and verified positioning of the guidance tool on the patient's anatomy. Second, provided is a registration component 76 spanning the femoral neck, the registration component 76 comprising a mating surface 78 (more clearly shown in FIGS. 7a to 7d) for accurate registration on the patient's anatomy. Third, optionally provided is a stability component 80 for additional stability during use. The body portion 68 of the guidance tool, in particular the guide component 70 may optionally include one or more locking keys 82 for use with a verification tool, as discussed below.

As mentioned above, the guidance tool 66 may take on any number of configurations, depending on the implementation. As such, in alternate configurations, the guidance tool 66 may be comprised of a combination of the above noted components. For example, while the guide component 70 is configured to serve as a drill guide, it may also be provided with a mating surface 78 for additional registration on the patient's anatomy. Additionally, the registration component 76, while comprising the mating surface 78 for registration on a patient's anatomy, may also comprise one or more guide channels 74 for receiving drill sleeves. As will be appreciated, the patient-specific guidance tool 66 is designed for intraoperative use, whereby the guidance tool 66 is fitted to the patient's anatomy. As indicated earlier, while the present embodiment is being presented within the framework of hip-resurfacing, the guidance tool and associated methodology/procedure for construction and implementation may be suitably applied to a range of surgical procedures, such as, but not limited to ankle, knee and shoulder surgery, spine fusion, craniomaxillofacial surgery, osteotomies, fracture treatment and fixation, scoliosis, wrist surgery, and mosaicplasty. In addition, for any one surgical procedure, particularly those during which multiple manipulations are necessary, it may be preferable to create and use a plurality of guidance tools. For example, a first guidance tool may facilitate a set of drilling trajectories, while a subsequently used second guidance tool may facilitate shaping. Using a plurality of tools will assist in keeping the size of the tool to a minimum, and should also serve to avoid an unnecessarily complicated design.

In certain circumstances, the registration component 70 of the guidance tool 66 may comprise a discontinuous mating surface 78, particularly if a portion of the imaging data is not suitable for rendering the surface detail of the patient's anatomy. In other instances, the registration surface 84 (see FIG. 6) of the patient's anatomy may not be suitable for incorporation into the registration component 76 of the guidance tool 66. In a guidance tool 66 comprising such a discontinuous mating surface 78, certain sections of the mating surface 78 may be voided in a manner that prevents interference with the patient's anatomy. For example, the discontinuous portions may be sufficiently recessed to clear the patient's anatomy.

In designing the patient specific guidance tool 66, a wide range of factors may be considered, so as to ensure the development of a specific customized product. For example, the guidance tool may be designed having regard to a chosen or preferred surgical approach or technique. For example, as one skilled in the art will appreciate, in hip resurfacing, the anterior-lateral approach is generally preferred to preserve a better blood supply to the femoral head, while the posterior approach serves to retain the capsular. The choice of anterior-lateral vs. posterior approach will have an overall impact upon the final design of the tool. Customization of the guidance tool based on a single chosen surgical approach has the advantage of simplifying the final design, as multiple surgical approaches need not be engineered into a single tool. As such, the patient-specific guidance tool need not be unnecessarily large, and can therefore be appropriately sized to reduce the invasiveness of the surgical procedure.

The guidance tool 66 is designed having regard to the specific registration surface 84 of the patient's anatomy, namely characteristic anatomical landmarks, bony structures and/or soft tissue (e.g., tendons, ligaments, etc.). For clarity, anatomical landmarks, bony structures and soft tissue are herein collectively termed "characteristic landmarks". The characteristic landmarks of the registration surface 84 are used in designing the mating surface 78 of the guidance tool 66, so as to register it in a specific position/orientation necessary to attain the desired drilling trajectory 58 determined during the pre-operative planning stage. The chosen surgical approach (e.g., anterior-lateral vs. posterior) may also have a bearing here, as certain characteristic landmarks may be exposed depending on the selected approach. As will be discussed below, the characteristic landmarks may also be used intraoperatively to verify the position of the guidance tool 66 when affixed to the anatomy. Any combination of characteristic landmarks (anatomical landmarks, bony structures, soft tissue, etc.) may be used for registering and/or verifying correct positioning of the tool on the patient's anatomy. This information is taken into consideration during the design of the guidance tool.

Figure 7A:
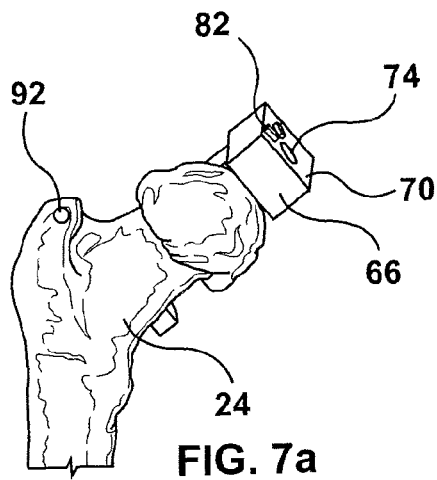
Figure 7B:
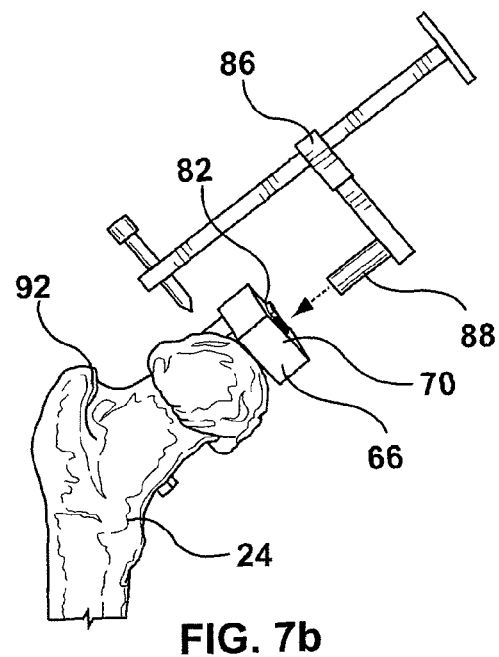
Figure 7C:
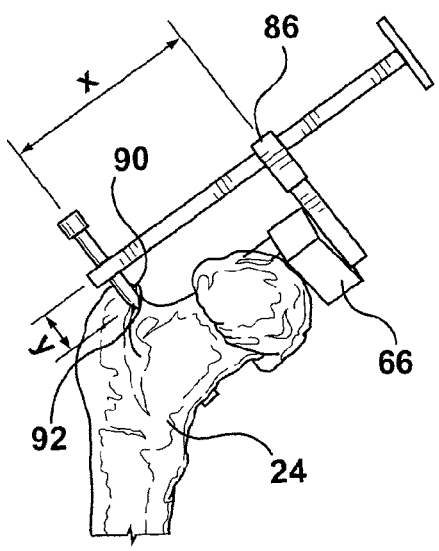
Figure 7D:
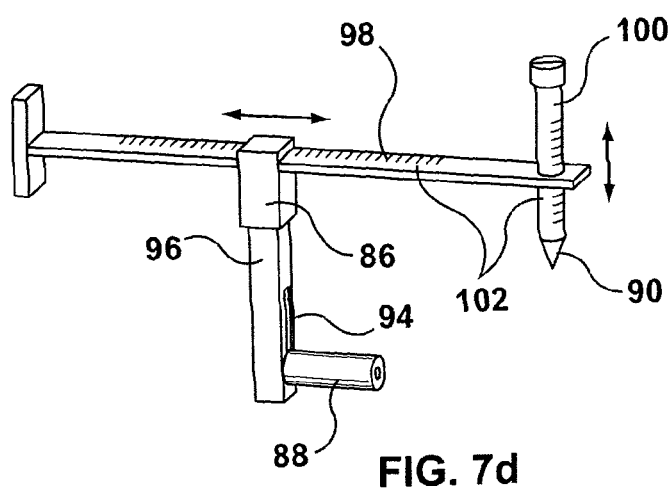
FIG. 7d is a perspective view of an embodiment of the verification tool used with the guidance tool to verify correct positioning of the guidance tool on the femur.

To verify the position/orientation of the guidance tool 66 on the patient's anatomy, and to verify that the correct preoperatively define trajectory is attained, the guidance tool 66 may be provided with a removable mechanical verification tool 86, as shown in FIGS. 7b through 7d. With the guidance tool 66 placed onto the patient's anatomy as shown in FIG. 7a, the verification tool 86 is configured to be removably attached to the guidance tool 66 by inserting the registration pin 88 of the verification tool 86 into the guide channel 74 of the guide component 70, as shown in FIG. 7b. The pointer 90 of the verification tool 86 can then be used, as shown in FIG. 7c, to locate one or more characteristic landmarks 92 that were preoperatively identified, so as to determine whether or not a proper positioning of the guidance tool has been established. To ensure accurate radial placement of the verification tool 86 relative to the longitudinal axis of the planned central pin trajectory 58, one or more locking keys 82 are provided on the guide component 70 to lock the verification tool in one or more predefined orientations. As shown in FIG. 7d, the verification tool 86 is provided with a recess 94 on the stem 96 for cooperating with the locking key 82 of the guide component 70, thereby locking the verification tool 86 in a fixed position. As will be appreciated, while a single characteristic landmark 92 may be used for position verification, the procedure may use a plurality of characteristic landmarks. As such, the guide component 70 may be configured with multiple locking keys 82, each corresponding to a particular landmark.

The verification tool 86 is used to indicate whether or not the guidance tool 66 is correctly positioned on the patient's anatomy, and whether or not the guidance tool establishes the preoperatively defined trajectory 58. In the event of a misalignment, the user is able to quantifiably gauge the extent of misalignment using one or more graduated sections provided on the verification tool 86. The graduated sections may include a scale such as a vernier or linear scale so as to allow measurement of the position of the guidance tool. For example, a graduated section may include a sliding ruler. In the embodiment shown in FIG. 7d, measurements along the longitudinal axis (x) of the planned central pin trajectory 58 are provided by a first sliding ruler 98, while radial measurements (y) are provided by a second sliding ruler 100 provided on the pointer 90. Graduations 102 (e.g., mm) are provided on each ruler so as to provide a numerical indication of how much and in which direction the guide is misplaced from the planned fitting position. The verification tool may provide further indicators to characterize the nature of the misalignment. For example, it may be useful to obtain an angular misalignment value, that is the angle between the anatomical landmark and the preoperatively defined position of the verification tool. As such, a protractor-like scaling on the verification tool and/or guidance tool would be provided to facilitate this type of measurement.

Misalignments of the guidance tool may arise due to a variety of reasons. For example, they may arise due to an error during the preoperative planning stage. Misalignments may also arise due to physiological changes in the patient, for example the formation of osteophytes on the registration surface. To realign the guidance tool, removal of the osteophytes may be all that is required. In other instances, the misalignment may require the use of a realignment sleeve, as discussed in greater detail below. To assist the use in determining the necessary course of action to realign the guidance tool, the user of the guidance tool 66 is preferably provided with a reference chart, table or realignment calculator. The reference chart, table or realignment calculator allows the user to determine an appropriate realignment trajectory based on the characteristics of the misalignment obtained from the verification tool, such that the preoperatively defined trajectory can be attained.

The following demonstrates an exemplary use of the verification tool. For each anatomical landmark $l_i$ chosen, a pair of values (x,y) is preoperatively determined, which describe the target location for the pointer of the verification tool. Intraoperatively during the verification of the guidance tool position, the verification tool is inserted into the guide channel and the values (x_m, y_m) are measured for the preoperatively determined anatomical landmark $l_i$. If the guidance tool is correctly placed in the preoperative defined position for all landmarks the measured values (x_m, y_m) would be identical to the preoperative determined values (x,y).

In case of misalignment, for one or more landmarks a deviation between intraoperative measured values and preoperative determined target values will occur. The characteristics of the misalignment, namely the direction and amount of misalignment of the landmarks can be used to identify a) position of registration-error, of b) plan of correction possibility (realignment). Based on this information the user can attempt an initial correction by, for example, removing osteophyte. If correction is not possible, the reference chart, table or realignment calculator is provided to navigate the user to the appropriate correction/realignment possibility.

The following example demonstrates the use of such a reference chart, table or realignment calculator using values obtained from the verification tool. For this exemplary implementation, two anatomical landmarks $l_1$ and $l_2$ were chosen. The preoperative defined (x,y) values for these landmarks are listed in Table 1.

TABLE 1

Preoperatively determined landmark coordinates

|  | x | y |
|---|---|---|
| $l_1$ | 92 mm | 21 mm |
| $l_2$ | 57 mm | 29 mm |

With the verification tool, the preoperatively determined anatomical landmarks are used to identify a misalignment. The direction and amount of the misalignment is determined.

Example 1

A set of exemplary intraoperative measured (x_m, y_m) values for both landmarks are presented in Table 2.

TABLE 2

Intraoperatively measured landmark coordinates

|  | x_m | y_m |
|---|---|---|
| $l_1$ | 92 mm | 23 mm |
| $l_2$ | 57 mm | 31 mm |

In this case, the deviation between the intraoperatively measured y_m values and the preoperatively defined y values indicate a misalignment in the direction of the frontal plane. The amount of deviation, defined as $$a = y\_m - y$$

is used to identify the amount and type of displacement. With respect to landmarks $l_1$ and $l_2$, the corresponding $a_1$ and $a_2$ values are calculated as follows:

$$a_1 = y\_m_1 - y_1 = 23 - 21 = 2$$

$$a_2 = y\_m_1 - y_1 = 31 - 29 = 2.$$

From this analysis, a translational misalignment is identified. Having regard to the reference table (Table 3), the suggested realignment is the use of a 2 mm translational offset in the inferior direction.

TABLE 3

Translational offsets for corrections in Frontal Plane

| | a | A | a | |
|---|---|---|---|---|
| 1 | −0.5 < a < 0.5 | 0.5 <= a < 1.5 | −1.5 < a = < −0.5 | ... |
| 2 | −0.5 < a < 0.5 | 0.5 <= a < 1.5 | −1.5 < a < = 0.5 | |
|  | No offset | 1 mm offset superior | 1 mm offset inferior | |

Where, a = y_m − y
x, y = preoperative defined values
x_m, y_m = intraoperative measured values

Example 2

A second set of exemplary intraoperative measured (x_m, y_m) values for both landmarks are presented in Table 4.

TABLE 4

Intraoperatively measured landmark coordinates

|  | x_m | y_m |
|---|---|---|
| $I_1$ | 92 mm | 21 mm |
| $I_2$ | 57 mm | 31 mm |

In this example the deviation between the amount of displacement between landmarks $l_1$ and $l_2$ identifies an angular displacement. With respect to landmarks $l_1$ and $l_2$, the corresponding $a_1$ and $a_2$ values are calculated as follows:

$$a_1 = y\_m_1 - y_1 = 21 - 21 = 0$$

$$a_2 = y\_m_2 - y_2 = 31 - 29 = 2$$

The difference (d) between $a_2$ and $a_1$ is determined as $$d = a_2 - a_1.$$

Accordingly, the difference is determined as follows:

$$d = a_2 - a_1 = 2 - 0 = 2$$

This angular displacement represents a 3° hyper-extension misplacement of the guide, requiring the use of realignment sleeve having a 3° flexion offset, as specified in the reference table provided in Table 5.

TABLE 5

Angular offsets for correction in Frontal Plane

| d | d | d | d |
|---|---|---|---|
| −0.5 < d <= 0.0<br>No offset | 0.0 < d <= 1.0<br>1° offset flexion<br>−1.0 =< d < 0.0<br>1° offset extension | 1.0 < d <= 1.5<br>2° offset flexion<br>−1.5 =< d < −1.0 | 1.5 < d <= 2.5<br>3° offset flexion |

Where, a = y_m − y, d = $a_2$ − $a_1$
x, y = preoperative defined values
x_m, y_m = intraoperative measured values Based on the preoperative planning of the guidance tool 66, and the selection of the anatomical landmarks 92 for use with the verification tool 86, the aforementioned reference chart or table can be preoperatively calculated, such that cross-reference of these misalignment values provides the realignment necessary to achieve the preoperatively defined trajectory 58. In a preferred embodiment, the realignment determination is provided by way of the realignment calculator, provided for example on a computer accessible within the operative environment.

The realignment is provided by way of a realignment sleeve, as will be discussed in greater detail below. With this approach to correct misalignments, the user is not left with having to approximate the correction, but rather is provided with a directed calculated correction based on a specific measurements made with the verification tool.

Figure 8B:
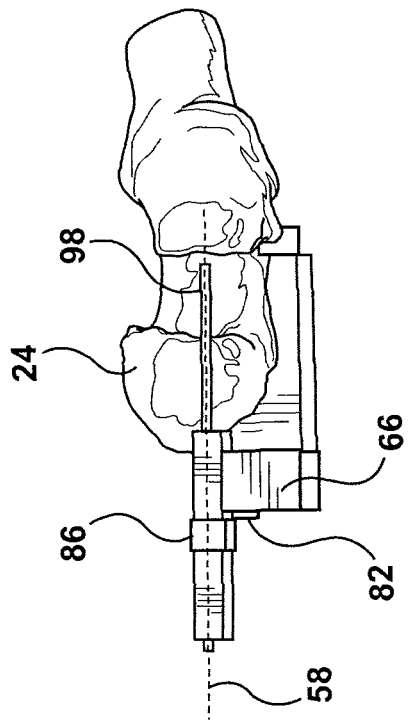
FIGS. 8a and 8b are perspective views of an embodiment of the verification tool in which it is used as a visual aid in verifying the planned trajectory.
Figure 8A:
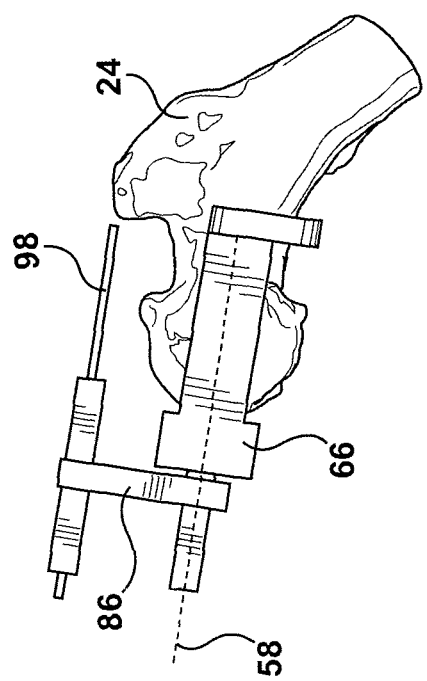

Since the first sliding ruler 98 is generally configured to be parallel to the longitudinal axis of the central pin, the verification tool 86 may also be used as a visual sighting aid to verify the chosen drilling trajectory 58 and planned axis alignment, as shown in FIGS. 8a and 8b. By disengaging the verification tool 86 from the locking keys 82 and rotating the verification tool 86 about the guidance tool 66, the user is able to visualise the trajectory 58 of the central pin with reference to the plane defined by the first sliding ruler 98, or alternatively a pin or guidewire inserted in place of the ruler. In some embodiments, the verification tool 86 may be configured to receive a separate pin or guide wire, also positioned parallel to the trajectory defined by the guidance tool. If it appears that a trajectory correction is necessary, suitable adjustments can be made as described in greater detail below.

The verification tool 86 may also be used intraoperatively to confirm that the selected femoral component size is appropriate by measuring the radial distance between the planned central pin trajectory 58 and the surface of the femoral neck. Alternatively, or in addition, this process can also be used to confirm that the planned trajectory is substantially centered within the femoral neck.

The verification tool 86 as presented above is removable, thus allowing it to be reused. Alternatively, the verification tool 86 may be incorporated as a permanently fixed, integral component of the guidance tool 66. As such, there would be no need for the verification tool locking keys as described above. In such a case, the verification tool could be machined to use the sliding rulers as discussed above, or constructed as a single purpose non-adjustable pointer for identifying a chosen characteristic landmark.

In the case of a removable verification tool 86, the tool may find further application once detached from the guidance tool. For example, the verification tool may be used to provide two or more references points that are preoperatively determined to line up with certain anatomical landmarks, or to provide a gauge for assessing fit. The verification tool, particularly where the tool is adjustable, can be set to a predefined setting that will enable verification that a particular point, for example on a prosthesis is correctly positioned at a preoperatively defined location relative to a preoperatively selected anatomical landmark. The verification tool may find further applications in which a measuring device or gauge is useful in the operative environment.

In instances where a plurality of guidance tools are used for a particular procedure, a separate verification tool may be configured for each guidance tool used. Alternatively, the verification tool may be used with the first guidance tool, with the positioning of subsequent guidance tools being verified relative to a common reference point as determined by the first guidance tool. For example, upon placement of the first guidance tool, the bone or cartilage may be marked using at least one reference point. During placement of each subsequent guidance tool, to ensure proper alignment, each subsequent guidance tool is verified against this at least one reference point.

Figure 9D:
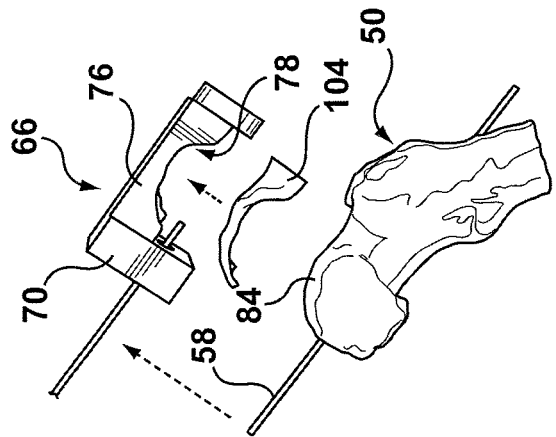
FIGS. 9a to 9d show a 3-D computer iso-surface model representing bone and/or soft tissue of the proximal femur, the series of illustrations showing a determined pin trajectory, a registration surface and a guidance tool comprising these features.
Figure 9C:
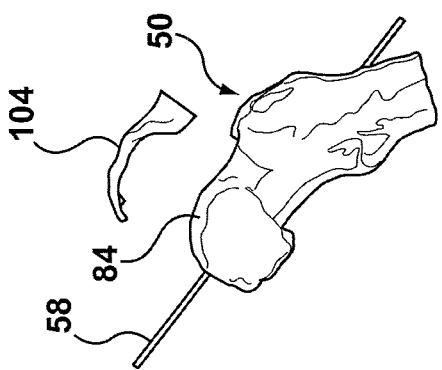
Figure 9B:
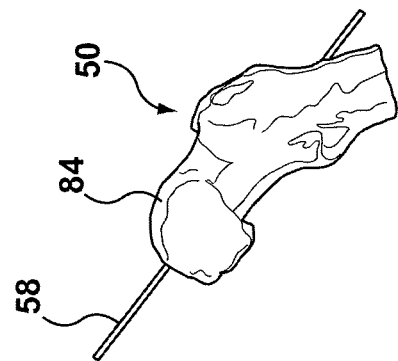
Figure 9A:
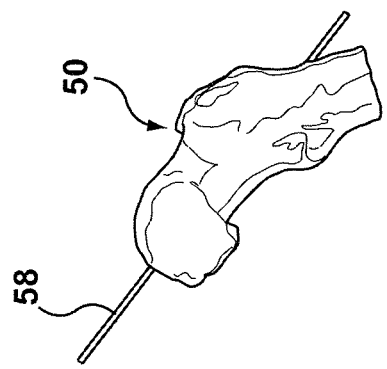
Figure 10:
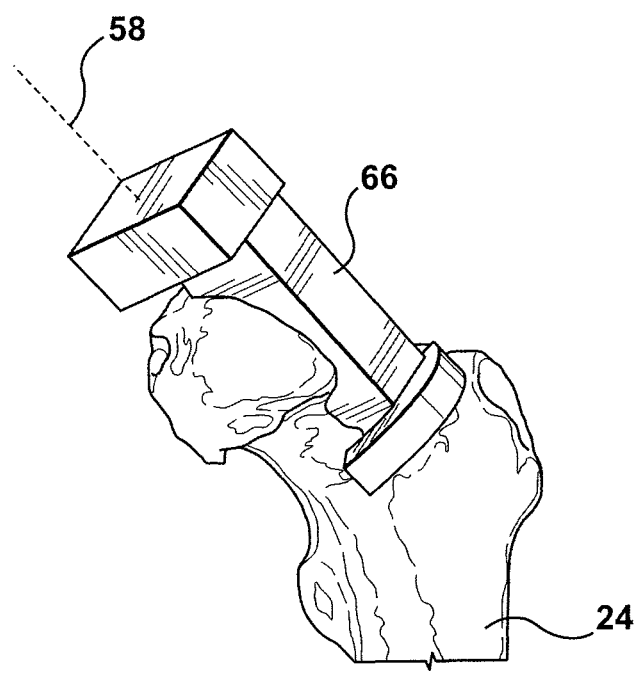
FIG. 10 is a perspective view of the femur, shown intraoperatively, with the guidance tool in position.

The general steps involved in pre-operative planning of the patient-specific procedure for hip resurfacing are represented in FIGS. 9a through 9d. As shown in FIG. 9a, based on medical imaging incorporating the patient's characteristic anatomical landmarks, the virtual 3-D iso-surface model 50 of the patient's anatomy is first created. The anatomical orientation/coordinates of the model are determined, the shaft/neck axis is registered, and the position and orientation of the femoral component is determined. FIG. 9a illustrates the planned trajectory 58 of the central pin, based on the established shaft/neck axis. In FIG. 9b, a selected portion of the patient's anatomy is analyzed to determine characteristic landmarks defining the registration surface 84, as well as tool positioning verification anatomical landmarks. As shown in FIG. 9c, an extracted surface image 104 of the registration surface 84 is created. At this point in the process, the trajectory 58 of the central pin and the characteristics of the mating surface 78 have each been separately established. In FIG. 9*d*, the trajectory 58 of the central pin and the characteristics of the mating surface 78 are combined into a single virtual guidance tool 66, wherein the planned trajectory 58 is governed by the guide component 70. As such, when used intraoperatively, the mating surface 78 of the tool 66 is positioned on and registered with the patient's anatomy, as represented in FIG. 10, thus providing the planned trajectory 58 for the central pin.

The aforementioned task of designing the patient-specific guidance tool during the preoperative planning stage is computer assisted using a custom software program. The software program is configured to design a specific and customized guidance tool by taking into consideration the various factors discussed above. In particular, the software program provides an interface enabling the user to analyze and identify the location of characteristic landmarks on the patient's anatomy, and design the guidance tool such that it positionally registers on the patient's anatomy in a predefined orientation. In addition, the software program helps the user avoid structures not suitable for registration of the guidance tool. For example, certain soft and/or unstable bony structures such as osteophytes are dismissed as viable registration points.

The creation of the patient-specific guidance tool using the aforementioned software is generally a two step process. In the first step, the software enables the user to plan the size, shape, position, and orientation of the guidance tool based on the patient's anatomy as determined in the initial medical imaging. In the second step, a 3-D representation of the guidance tool is calculated comprising the various characteristics specific to the patient's unique anatomy. The calculated 3-D representation is then saved in a 3-D model format, such as a stereolithographic format (e.g., standard tessellation language (STL-format)).

The first step of patient-specific guidance tool planning is accomplished using available software packages such as Qt (Trolltech ASA, Oslo, Norway; www.trolltech.com) and Coin3D (Systems in Motion AS, Oslo, Norway; www.coin3d.org). Qt allows high-performance cross-platform GUI (graphical user interface) development, while Coin3D is a high-level 3D graphics toolkit for developing cross-platform real-time 3D visualization software. It will be appreciated, however, that one skilled in the art could implement other suitable software programs in place of those mentioned above.

Software suited for the first step of patient-specific guidance tool planning preferably offers the following functions: a) establishment and loading of the 3-D surface model of a patient's anatomy; b) establishment and loading of surgical planning; c) planning of locking keys; and d) designing of patient-specific guidance tool.

The following paragraphs describe an example of patient-specific guidance tool planning as applied to hip resurfacing. Variations of this procedure will be apparent to one skilled in the art.

Based on preoperative medical imaging, the 3-D surface model of a patient's anatomy is loaded and displayed to the user. Next, the determined trajectory of the central pin is loaded and displayed as a cylinder. The guidance tool is then designed, in this case as three different parts. First, the registration component is oriented along the femoral neck and contains the mating surface which mates the registration surface of the patient's anatomy. Second, the stability component is oriented around the lateral femoral neck, and contains a mating surface that registers with at least a portion of the anterio-lateral or posterior-lateral neck. Third, the guide component provides the guide channel for the drill sleeves.

During patient-specific guidance tool planning, the user chooses the size, position and orientation of the registration component. To facilitate the design process, a rectangular prism or cube representing the registration component is displayed, allowing the user to modify width, height and length, as deemed necessary to achieve a proper sizing and fit. The user can further define the final position by altering the position and rotation of the rectangular prism or cube around the central pin axis.

For planning of the stability component a virtual ring-segment is displayed, which is attached on the lateral side of the registration component. The user can modify the radius, angle, width and height of this ring segment and change its position and orientation, so as to achieve a proper sizing and fit.

For planning of the guide component a virtual cube is displayed, which is attached on the medial side of the registration component. Similar to the previous two components, the user can modify width, depth, and height of this cube, so as to optimize the sizing and fit.

At this stage, the planning must also consider the verification tool and the associated locking keys. It is during this planning that the user selects one or more anatomical landmarks on the femoral model that will align with the verification tool. As described above, the alignment of the verification tool is governed by the locking keys. As such, based on the location of the anatomical landmarks, and the configuration/size of the verification tool, the positioning of the locking keys on the guide component is established.

In the second step wherein a 3-D representation of the guidance tool is calculated, the mating surfaces for the registration component and stability component of the guidance tool are calculated. In one exemplary methodology, the registration component and stability component are represented each as a set of 6 planes, which are defined by a bounding box. To determine the registration surface of the patient's anatomy, the surface representation of the bone is intersected with all six planes. For all resulting triangles the normal vectors are inverted and the mating surface is saved in a triangulated format.

For the final calculation of the registration and stability components, both virtual representations (cube and ring-segment) are saved as volumetric objects (sets of tetrahedrons). An algorithm is then used to intersect each volumetric object along the calculated mating surface. During this calculation the distance of each tetrahedron with respect to the mating surface is determined. Tetrahedrons which are intersected by the surface are split in two sets of tetrahedrons, corresponding to those below and above the surface. Finally all tetrahedrons above the surface are combined into one volumetric object and this object is converted into a surface model. The result is the surface representation of the registration and stability components of the guidance tool, which contains the mating surface complementary to the registration surface of the patient's specific anatomy.

For determination of the guide component, in particular the guide channel, the surface of a cylinder is modeled, which is oriented along the determined pin trajectory. The outer shell of the guide component and the locking keys are modeled as a rectangular prisms or cubes. The guidance tool is determined by combining these models.

The mating surfaces which are integrated into the guidance tool allow intraoperative registration of the tool to the characteristic landmarks of the registration surface of the patient. The anatomical registration surfaces must provide sufficient features to allow a precise fit of the tool to the anatomy. Location and size of the mating surfaces are defined by the shape, size, position and orientation of the guidance tool. To avoid intraoperative problems during fitting of the guidance tool to the anatomy, the mating surfaces can be evaluated for their quality of fit during preoperative planning of the guidance tool.

Quality of fit may be assessed by examining registration features (i.e., characteristic landmarks) of the registration surface and/or the mating surface. Various publications in the area of registration during computer-assisted surgery provide methods to evaluate registration features (Ma, B., Ellis, R. E. "A point selection algorithm based on spatial-stiffness analysis of rigid registration", Computer-Aided Surgery, 2005 July; 10(4): 209-223; Simon, D A. "Fast and accurate shape-based registration", PhD thesis, Carnegie Mellon University, Pittsburgh, Pa., December 1996). For clarity and by way of example only, the quality of fit of a mating surface can be determined in the following way. Virtual copies of the mating surface are created. To each of these copies a different error-transformation is applied and a surface-based registration algorithm is used to determine the transformation between this modified mating surface and the corresponding registration surface of the anatomy (Best, P., McKay, N. "A method for registration of 3-D shapes.", IEEE Trans. Pattern Anal. 1992, 14(2): 239-256). After the calculated transformation is applied to the modified mating surface copy, the distance between this mating surface and the original mating surface is calculated and saved as an error value. A chosen mating surface has sufficient registration features if the error values for all copies of the mating surface are below a predefined threshold. The error value is used to determine a figure of merit, which is indicative of quality of fit of the guidance tool to the patient's anatomy.

The figure of merit may also be representative of the level of invasiveness of the procedure. For example, the figure of merit may represent an optimization of factors including tool fit and level of invasiveness. For example, reducing tool size results in a less invasive procedure but a smaller tool size may also reduce quality of fit. As will be appreciated, the figure of merit is provided by the software, whereas the manipulation of the size, orientation, etc. is the designer's choice based on what the designer is trying to achieve in designing the tool.

An advantage of the patient-specific procedure and resultant guidance tool, which may be applied to any bone and joint surgical procedure, is that the user may customize the tool, for example by selecting a desired surgical approach (e.g., an anterior-lateral approach versus a posterior approach) which best suits the users ability and/or the needs of the patient.

Once the design is completed, the computer model data is saved in a stereolithographic format (e.g., STL) suitable for subsequent guidance tool manufacture. Alternatively, other formats may be used as would be apparent to one skilled in the art.

In the present embodiment, the subsequent manufacturing of the individual patient-specific guidance tool implements a rapid prototyping machine, such as the Dimension SST 3-D printer provided by Stratasys, Inc (Eden Prairie, Minn.). One will appreciate, however, that other suitable rapid prototyping machines may be used to manufacture the individual patient-specific guidance tool. In such a process, rapid prototyping takes the design of the patient-specific guidance tool and transforms it into virtual cross sections, followed by the creation of each cross section in physical space. The process continues through the various cross-sections until the physical model is finished. While a variety of metallic and non-metallic (e.g., polymers) materials may be used in rapid prototyping methods to make the guidance tool, the present embodiment is fabricated from acrylonitrile butadiene styrene (ABS). Following manufacture, the guidance tool is readied for use, which generally comprises sterilization and packaging using known methodologies.

In another embodiment, the patient-specific guidance tool may be manufactured intraoperatively in real time using computer assisted tool generation.

Figure 11A:
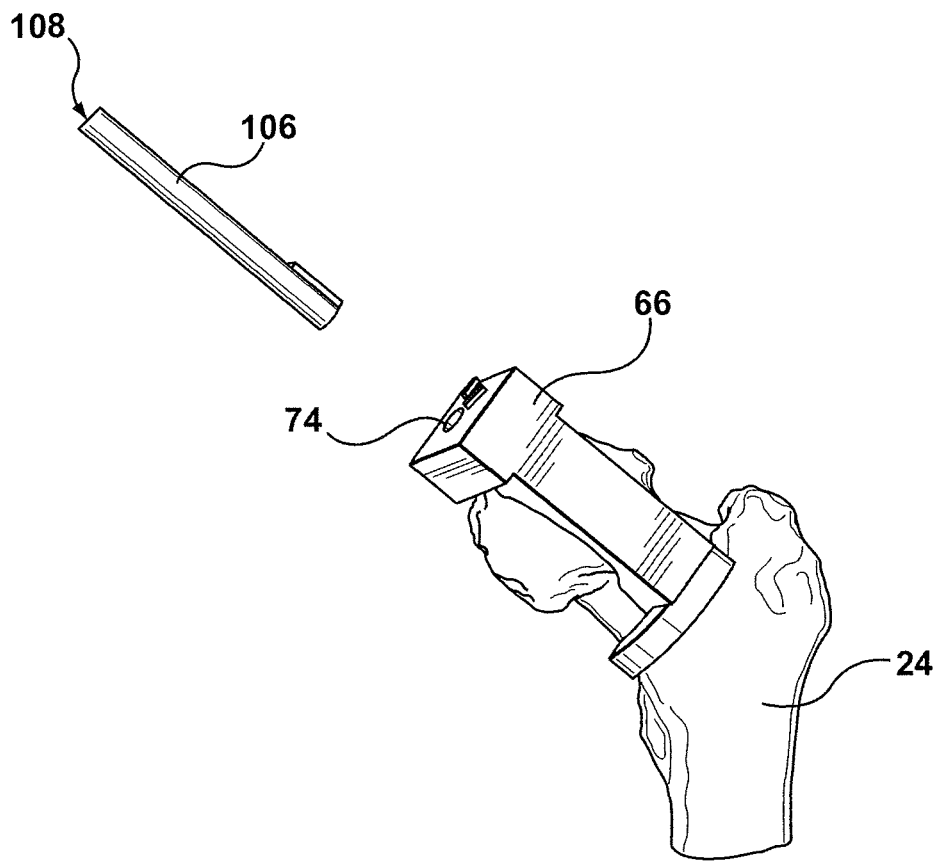
FIGS. 11a and 11b are perspective views of the femur with the guidance tool in position, wherein the guidance tool is readied for guiding the central pin into the femoral head.
Figure 11B:
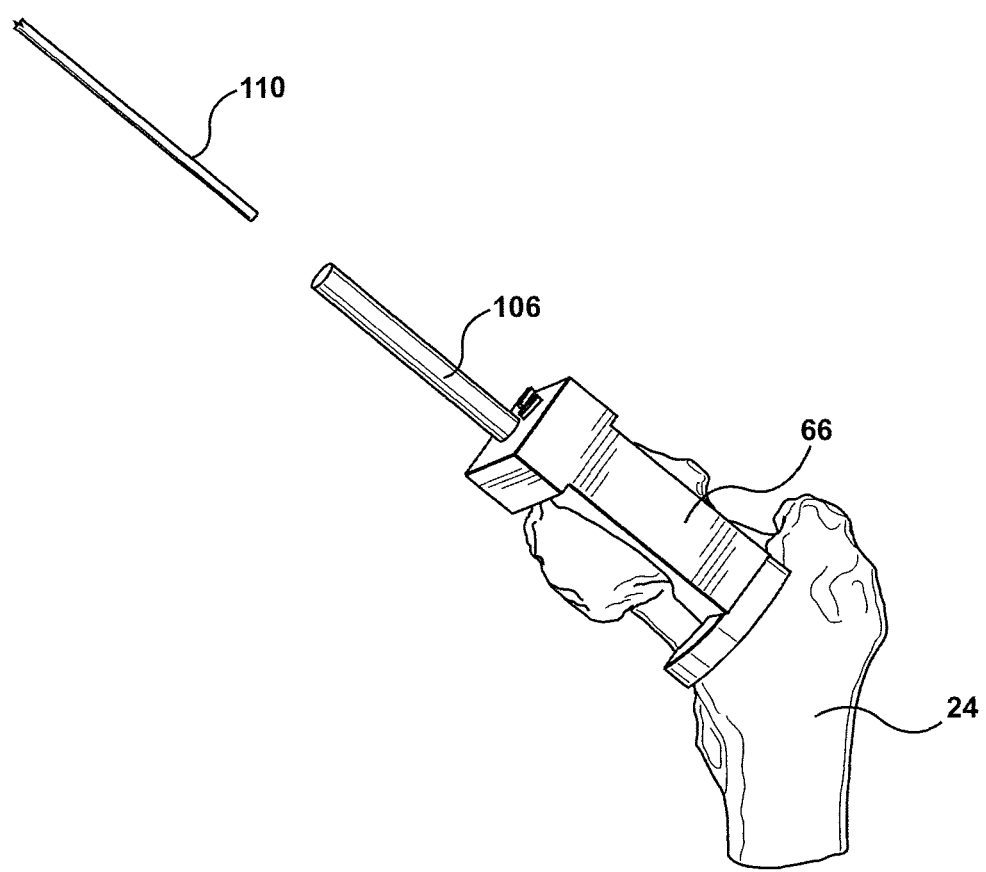

In use during hip resurfacing, following conventional surgical procedures known in the art, the femur is dislocated from the acetabulum. The patient-specific guidance tool 66 is then placed onto the desired part of the patient's anatomy as shown in FIG. 11*a*, having regard to the positioning and fit of the mating surface of the guidance tool relative to the corresponding registration surface of the patient's anatomy. While the guidance tool 66 may be fastened to the femur using suitable fasteners (e.g., pins, screws, etc), the guidance tool may alternatively be held in place manually by hand, or with suitable straps, clamps, zip-ties or elastic fasteners (e.g., elastic bands). Once registered to the bone, the verification tool 86 is used to verify the correct positioning of the guidance tool. With correct positioning verified, a drill sleeve 106 is inserted into the guide channel 74, as shown in FIG. 11*b*. The sleeve 106 provides a guide hole 108 for drilling and/or insertion of the central pin 110 at the planned central pin trajectory 58. The sleeve 106 is preferably a surgical grade metal, including but not limited to surgical grade stainless steel and titanium.

Figure 12A:
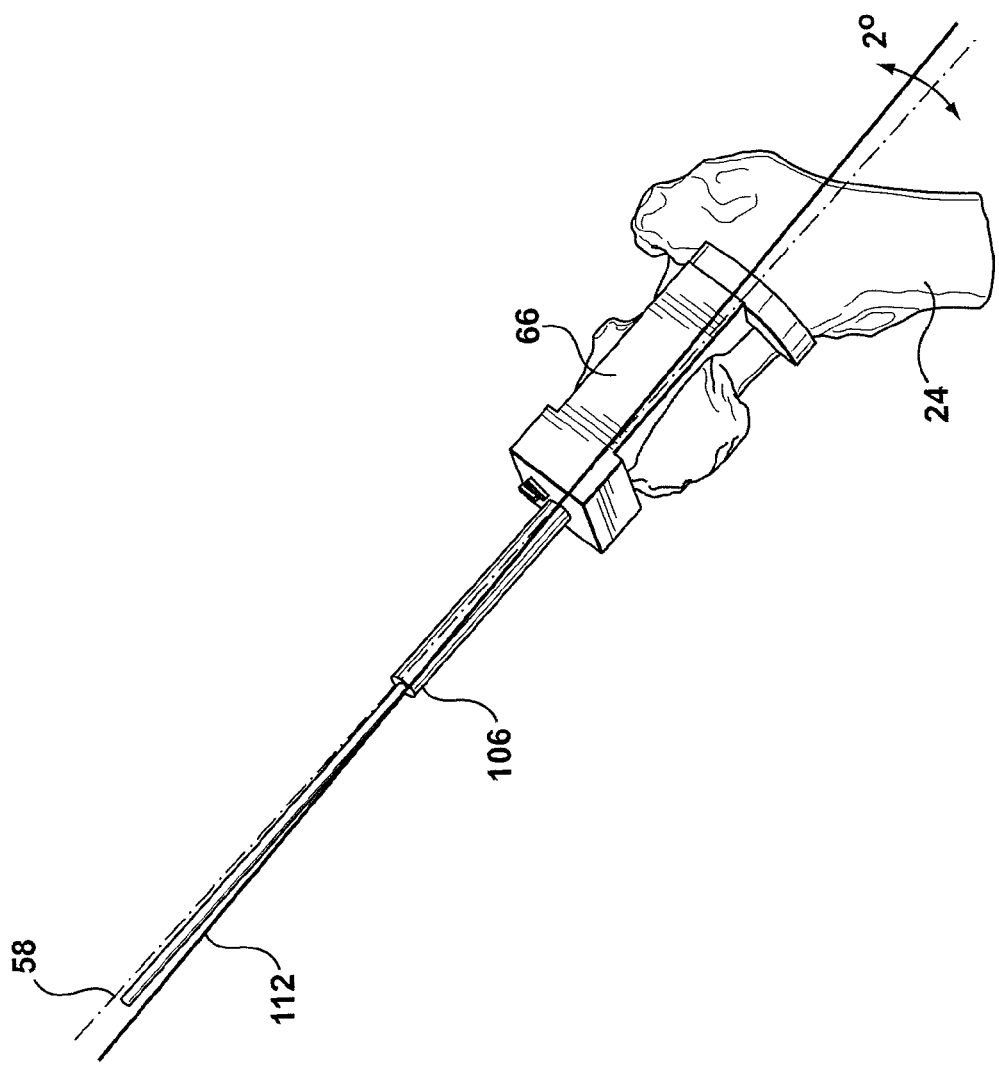
FIG. 12a illustrates a misalignment of the drilling trajectory.
Figures 12B, 12C:
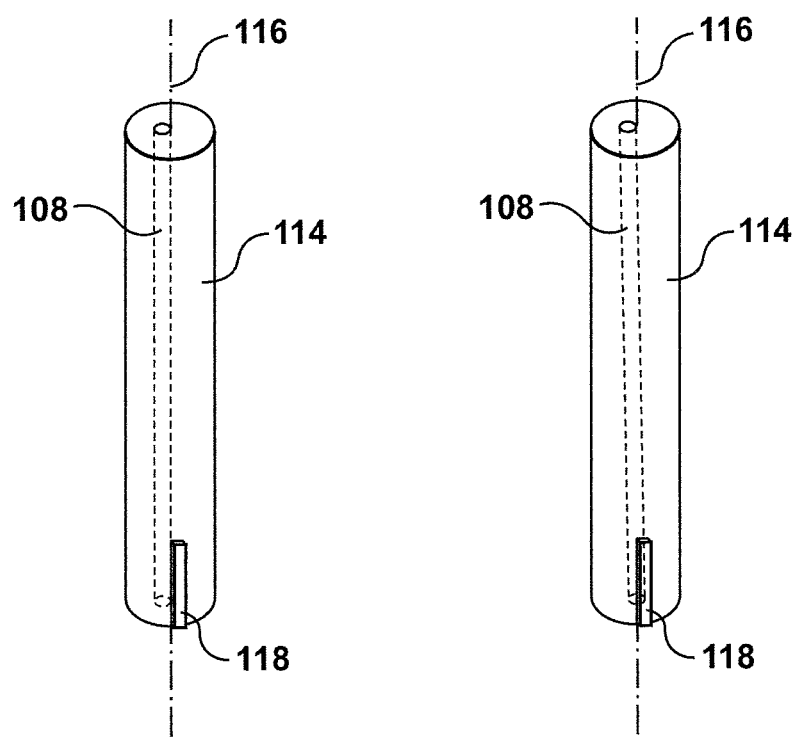
FIGS. 12b and 12c are perspective views of alternate drilling sleeves for use with the guidance tool wherein the guide holes are offset from the central axis.

During intraoperative use, as discussed above, it may be necessary to alter the trajectory 58 of the central pin, either due to a misaligned guidance tool as identified by the verification tool, or due to decisions made in the operating room. An exemplary misalignment 112 of 2° from a preoperatively defined trajectory 58 is shown in FIG. 12*a*. Should realignment or alteration of the trajectory of the central pin be necessary, realignment sleeves as shown in FIGS. 12*b* and 12*c*, can be used to drill holes that are offset by a known amount or are in a different orientation. For example, the realignment sleeve 114 shown in FIG. 12*b* has the guide hole 108 translationally offset from the central axis 116 of the sleeve, while the realignment sleeve 114 shown in FIG. 12*c* has an angled guide hole 108. Guide hole 108 translational offsets may be anywhere from 0 to 5 mm from the central axis 116. For example, the offsets are provided in 1 mm increments (e.g., 1 mm, 2 mm, 3 mm, 4 mm, 5 mm). Alternatively, the offsets are provided in 0.5 mm increments (e.g., 0.5 mm, 1.0 mm, 1.5 mm, 2.0 mm, 2.5 mm, 3.0 mm, 3.5 mm, 4.0 mm, 4.5 mm, 5.0 mm). Still further alternatives with smaller increments may be provided such as 0.1 mm increments, or 0.05 mm increments. Angled offsets from the central axis 116 may be anywhere from 0 to 5°. For example, the angled offsets are provided in 1° increments (e.g. 1°, 2°, 3°, 4°, 5°). Alternatively, the angled offsets are provided in 0.5° increments (e.g., 0.5°, 1.0°, 1.5°, 2.0°, 2.5°, 3.0°, 3.5°, 4.0°, 4.5°, 5.0°). Still further alternatives with smaller increments may be provided such as 0.1° increments, or 0.05° increments. Realignment sleeves 114 with combined translational offsets and angled offsets may also be provided in which the aforementioned dimensional characteristics would be applicable. Further, the drill sleeves 106 (and realignment sleeves 114) may be configured with a stop or other suitable mechanism to precisely control the depth of the pin placement. To ensure the drill sleeve 106 (and realignment sleeves 114) remains in a fixed position, the sleeves may be indexed relative to the guidance tool. For example, the drill sleeve 106 (and realignment sleeve 114) may be provided with a keyed surface 118 that cooperates with a receiving channel (not shown) on the guidance tool 66. The keyed surface 118 ensures the placement of the drill sleeve 106, in particular the realignment sleeve 114 in the preoperatively defined anatomical direction of the femur to ensure the corrections are performed in the desired direction (i.e., varus/valgus, anterior/posterior, etc.).

To facilitate the above-noted correction, as discussed above with reference to the verification tool, a reference chart, table or realignment calculator may be provided to assist in choosing the proper realignment sleeve to achieve the preoperatively defined trajectory. The choice of the correct realignment sleeve is based on the quantified misalignment as determined using the sliding rulers of the verification tool. The misalignment values are cross-referenced to the reference chart or table, or are inputted into the realignment calculator, and an appropriate realignment sleeve 114 is identified.

To further facilitate the above-described use, it may be advantageous to provide the operating room personnel with a model of the patient's anatomy. For example, the model may be provided as a paper printout, a screen image on a monitor in the operating room, or preferably a physical model. In certain circumstances, during intraoperative use, the user may find that the guidance tool is not fitting correctly to the patient's anatomy. For example, if a period of time passes between the initial medical imaging and the intraoperative procedure, the patient's anatomy could develop osteophytes that affect the overall fit of the guidance tool. Providing a model, in particular a physical model of the patient's anatomy, could facilitate the troubleshooting process in the event of guidance tool misalignment, if necessary.

To further enhance the adjustability of the guidance tool 66, the guide component 70 may be adjustable relative to the registration component 76. For example, in some embodiments, the guide component 70 may be detachable or configured to be loosened from the registration component, whereby the guide component 70 can be subsequently retightened in a slightly realigned position. The capability of being realigned can be provided, for example, by way of slotted or oversized holes through which suitable fasteners would be used.

Figure 13:
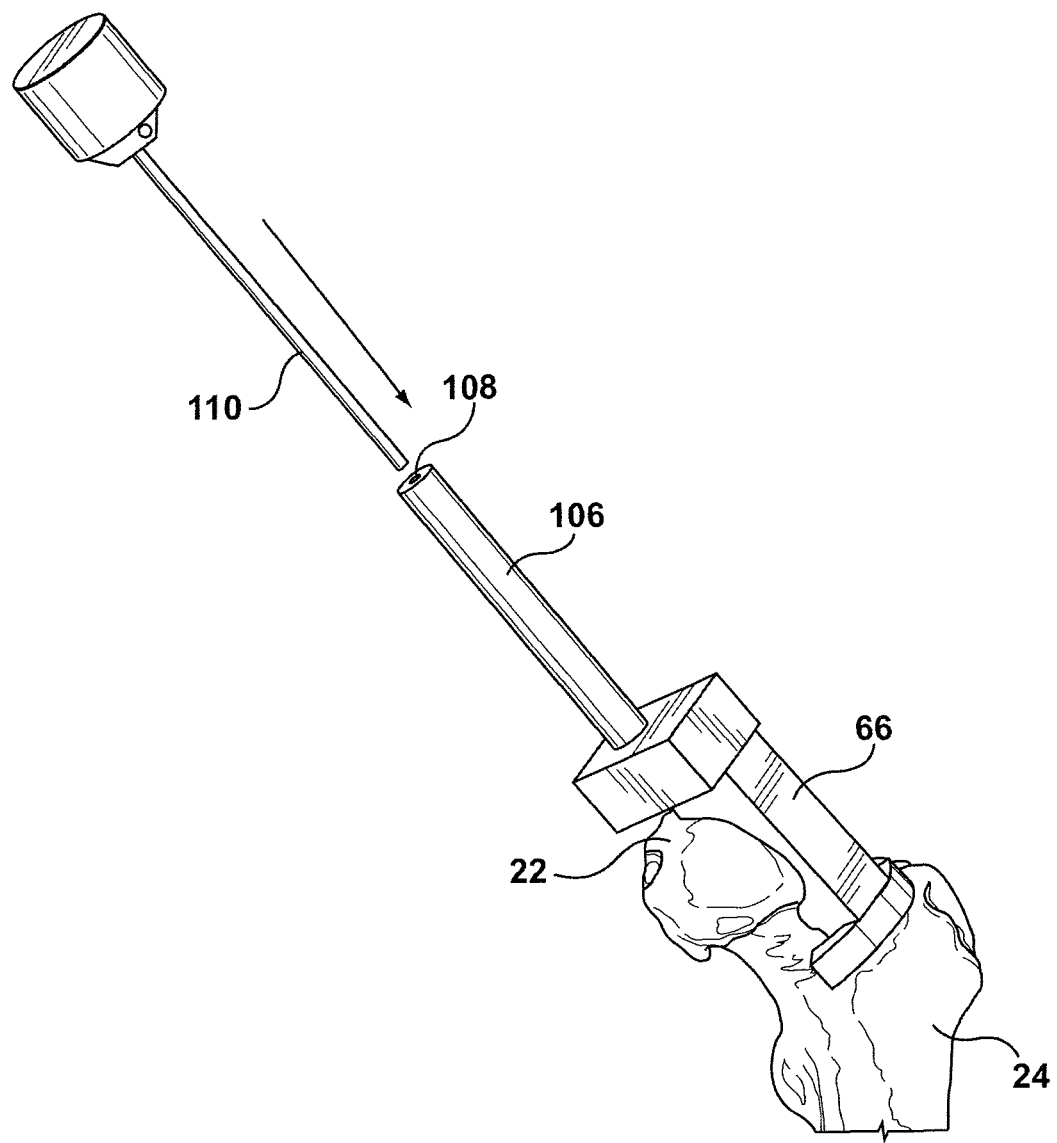
FIG. 13 is a perspective view of the femur with the guidance tool in position, wherein the central pin is being inserted into the drill sleeve for threaded insertion into the femoral head.

With the guidance tool 66 set in proper position/orientation, and the correct drill sleeve 106 or realignment sleeve 114 in place, the central pin 110 can be drilled into the femoral head 22 using drilling methodologies known in the art, as generally shown in FIG. 13.

Once the pin 110 is placed in the femur 24, the drill sleeve 106 (or realignment sleeve 114) is removed over the pin and the tool 66 is removed from the bone. The hip resurfacing procedure then continues according to instructions and/or training provided by the implant manufacturer.

As previously indicated, for the purposes of discussion, the patient-specific procedure and resultant guidance tool described above is exemplified having regard to hip resurfacing. One skilled in the art will appreciate that the above-noted patient-specific procedure and resultant guidance tool may find application in other surgical procedures, for example, knee, ankle and shoulder surgery, spine fusion, craniomaxillofacial surgery, osteotomies, fracture treatment and fixation, scoliosis, and wrist surgery.

Figure 14:
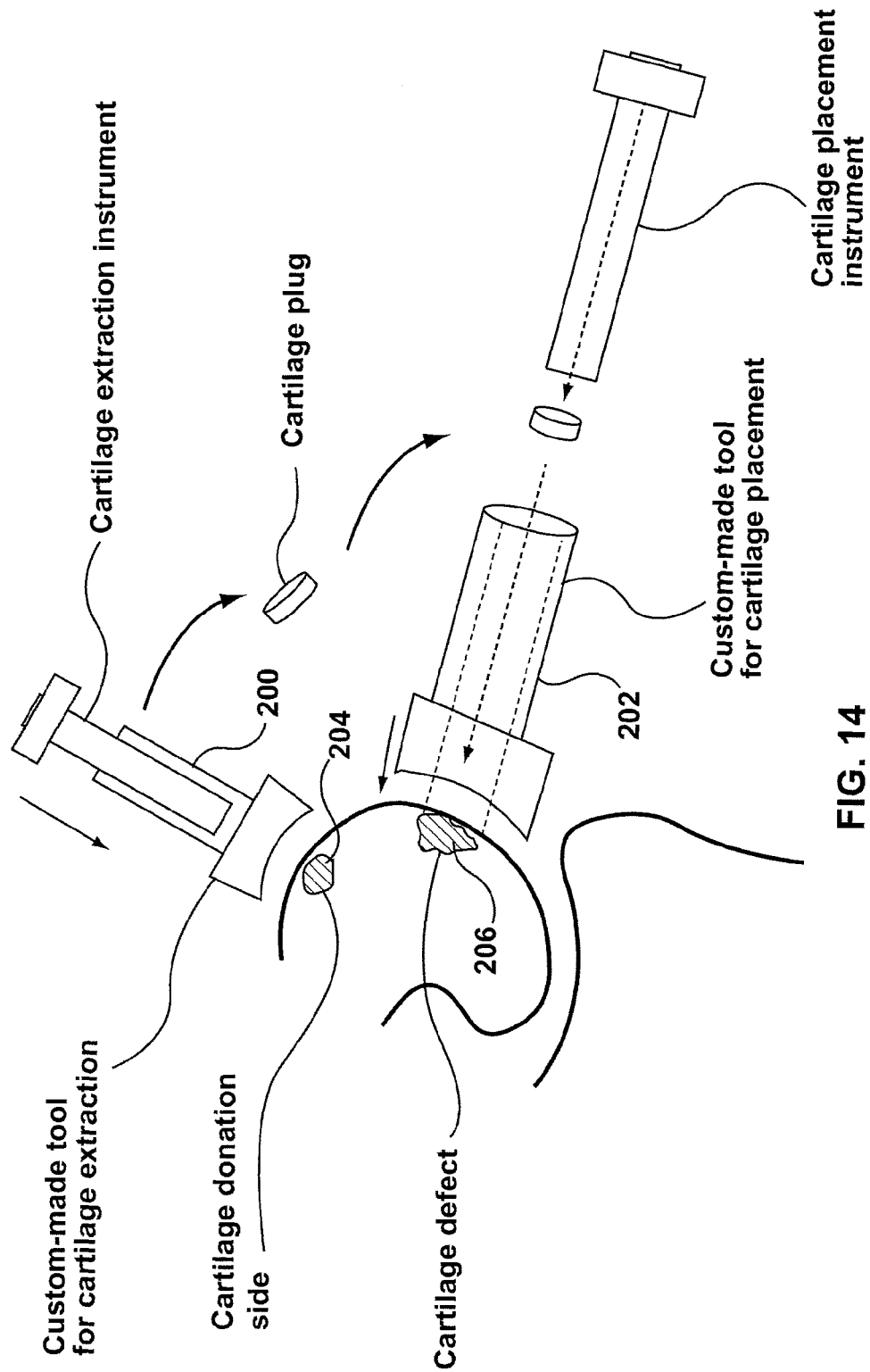
FIG. 14 is an schematic representation of how a guidance tool can similarly be used in mosaicplasty.

FIG. 14 shows an embodiment in which the preoperative procedure/methodology and resultant guidance tool is used in mosaicplasty, a form of therapy designed to replace the articular cartilage of the highly loaded surface of a joint that has been damaged by trauma or arthritis. Damaged articular cartilage in weight-bearing areas, for example the knee, is not only painful for the patient, but also limits the range of motion (ROM) and therefore has a great effect on the patient's quality of life. Surgical treatment is often the only treatment option, as the self-healing potential of articular cartilage is quite limited.

One treatment technique is the transplantation of multiple autologous osteochondral plugs from a donor region into the damaged region. For long term success of this procedure, the transplanted plugs should reconstruct the curvature of the articular surface. As such, many parameters including size, height, position, orientation and rotation of the plugs, as well as number and pattern of the plugs must be considered.

As generally represented in FIG. 14, mosaicplasty traditionally involves two guidance tools 200, 202, the first 200 being used on the donor site 204 to extract cartilage material, the second 202 being used on the receiver (damaged) site 206 to ensure correct positioning of the extracted cartilage.

Figure 15B:
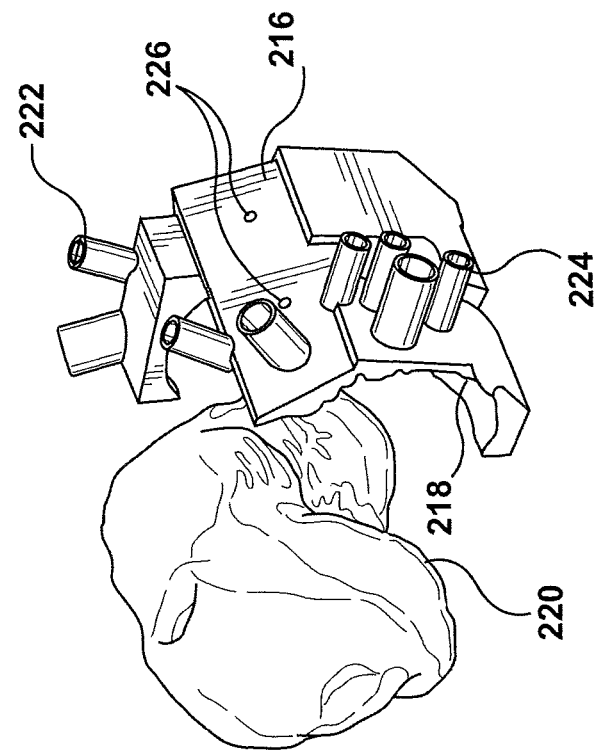
FIGS. 15a and 15b provide an illustration of how a guidance tool can be used in mosaicplasty of the knee.
Figure 15A:
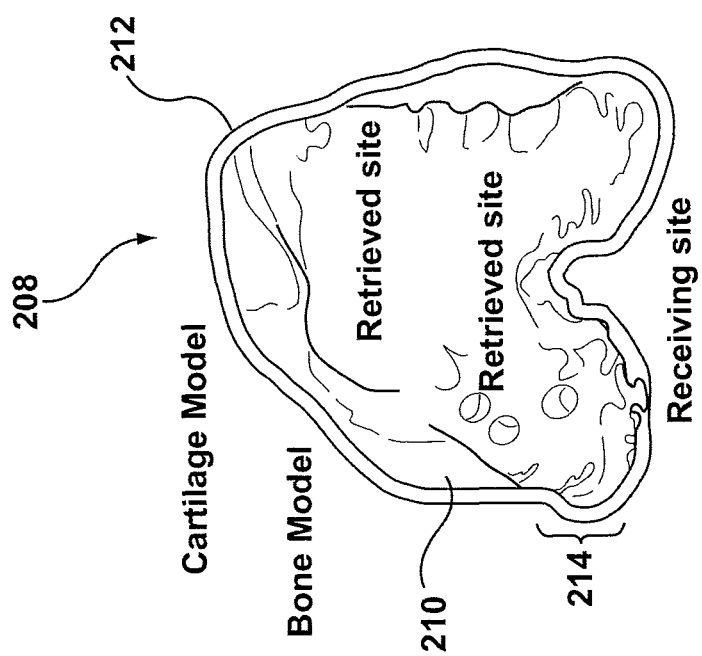

In the following exemplary embodiment of mosaicplasty of the knee, as described above for hip resurfacing, the patient is subjected to preoperative medical imaging by one or more of CT, MRI, ultrasound, X-ray, etc. to reconstruct the knee's bony anatomy, cartilage thickness, and an outline of the cartilage defect. As shown in FIG. 15a, a virtual 3-D iso-surface model 208 of the knee is computed, containing a bone model 210 and a transparent layer of cartilage 212. The damaged cartilage region 214 is next virtually restored by modifying the cartilage defects. The modified model is then used as the template for preoperative planning of mosaicplasty, using the aforementioned software. For each plug, the user can modify radius, height, position and orientation in the donor and receiving (damaged) areas. A graphical user interface allows the user to plan and evaluate the quality of fit of the final virtual guidance tool.

To transfer the final plan into intraoperative use, the patient-specific, sterilizable, plastic guidance tool 216 is formed using rapid prototype technology. As shown in FIG. 15b, the guidance tool 216 includes a mating surface 218 complementary to the articular registration surface 220 of the knee, enabling correct positioning of the tool 216 on the knee, thereby ensuring a precise transformation of the preoperative plan into the intraoperative surgical field. For each plug, two instrument guides may be incorporated in the guidance tool. For example, on the donor side of the guidance tool, a donor guide 222 is positioned to orient a plug cutting instrument with respect to the preoperative planning. To ensure the planned height of the plug, it is preferable to use a predefined height mark on the cutting instrument for alignment with the top edge of the guide. In a similar way, a guide 224 on the receiving (damaged) side of the guidance tool 216 is provided to facilitate navigation of the tools for preparation and transplantation of the plug into the damaged area. Both guides 222, 224 are preferably designed with instrument alignment marks to ensure that the rotation of the plug follows the planned curvature of the articular surface.

In some circumstances, the damaged anatomy may cover a sizable area. For example, it is not uncommon to have a cartilage defect of 2×3 cm on the medial site of the knee. To repair such a defect, a plurality of autologous osteochondral plugs are generally required, the diameters of which range from 4 mm to 8 mm.

For such a procedure, to facilitate intraoperative navigation, it may be advantageous to use three separately formed patient-specific guidance tools. Each of the guidance tools serve to guide the harvesting and insertion of 2-4 plugs. As previously mentioned, in instances where multiple guidance tools are used, a separate verification tool may be used for each guidance tool. Alternatively, the first guidance tool may be configured for use with a verification tool, while positioning of subsequent guidance tools is verified using a set of reference points, common to each of the guidance tools. For example, as shown in FIG. 15b, the guidance tool 216 provides two reference points 226 that allow for marking of the cartilage upon placement of the first guidance tool. During subsequent steps, alignment of a second guidance tool (not shown) to these reference marks 226 ensures that the second guidance tool is aligned to the first guidance tool; the positioning of the second guidance tool is verified. As each tool is placed upon the anatomy, alignment with the reference points ensures correct positioning of the guidance tool. With the guidance tool facilitating navigation, the procedure itself may be conducted using conventional cartilage repair systems, for example the COR cartilage repair system (Depuy Mitek Inc., a Johnson and Johnson company, Warsaw, USA).

The preoperative planning and guidance tool provides a time-efficient, accurate, cost-effective and easy to use method of articular cartilage reconstruction, particularly in instances involving multiple autologous osteochondral plugs.

Figure 16B:
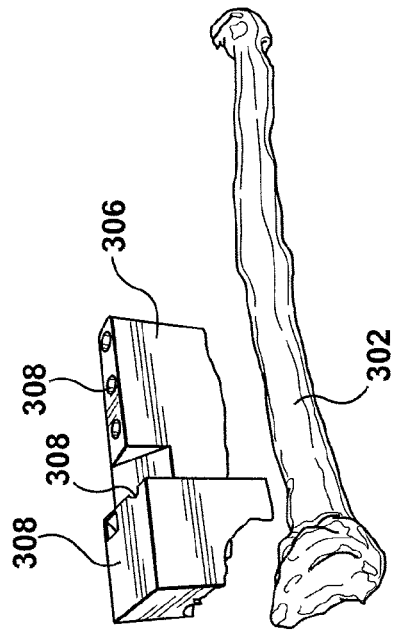
FIGS. 16a through 16d are illustrations of how a guidance tool can similarly be used in distal radius osteotomy.
Figure 16D:
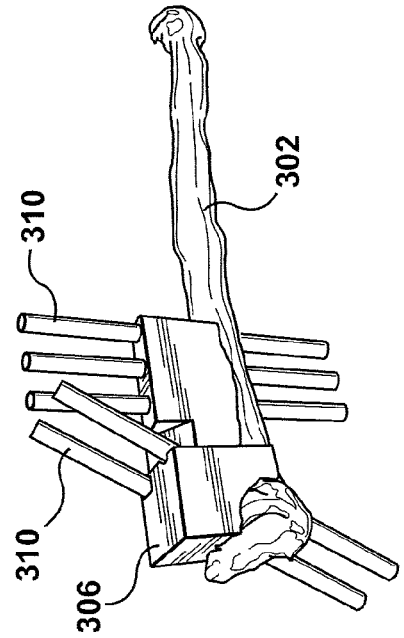
Figure 16A:
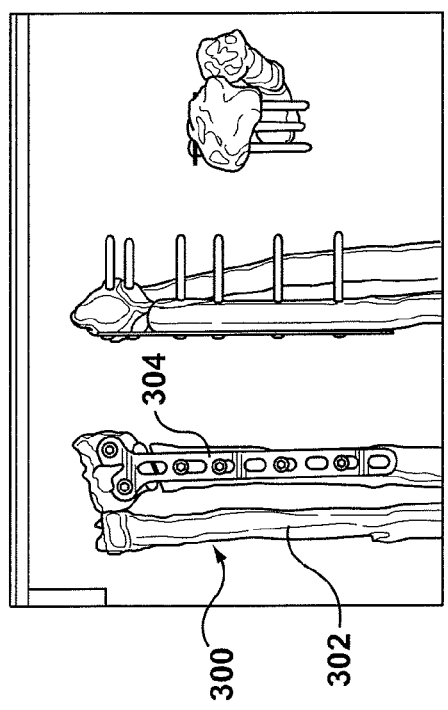
Figure 16C:
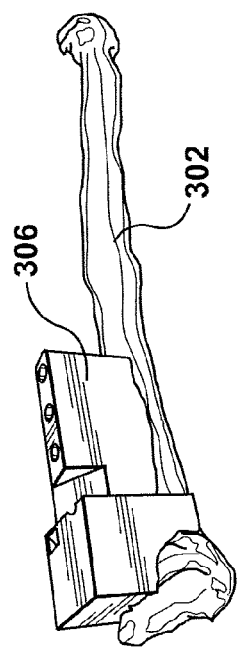

FIGS. 16a through 16d provide an embodiment in which the preoperative procedure/methodology and resultant guidance tool is used in distal radius osteotomy. An osteotomy is a surgical procedure to realign a bone in order to change the biomechanics of a joint, especially to change the force transmission through a joint. For distal radius osteotomy, a 3-D iso-surface model 300 of the radius 302 is created (from CT-data, and/or other suitable medical imaging) and the osteotomy is performed virtually (FIG. 16a). A model of the plate 304 is virtually placed on the proximal and distal ends of the virtually corrected radius 302. The screw positions and orientations of the plate are saved and transformed onto the original radius (non-fractured). A patient-specific guidance tool 306 is created (see FIG. 16b) in accordance with the procedure/methodology described above, which provides guide mechanism 308 for guided drilling of distal and proximal screw holes. During the surgery, the distal end of the radius is surgically exposed and the guidance tool 306 is positioned, as shown in FIG. 16c. Following verification using a verification tool, using drill sleeves (or realignment sleeves) inserted into the guidance tool 306, the user drills the screw holes into the radius 302, at the preoperatively planned trajectories 310 shown in FIG. 16d. The procedure may further use a second guidance tool (not shown) to facilitate the shaping of the distal surface using a Forstner drill bit, or other suitable tool. The guidance tool 306 may be configured to facilitate both the position/location and depth of milling in the shaping steps of the osteotomy. After the shaping is complete, the guidance tool 306 is removed and the surgeon performs the osteotomy in the conventional way. The plate, for example a Synthes 3.5 mm locking compression plate 304, is fixed using the preoperatively planned screw holes.

Figure 17B:
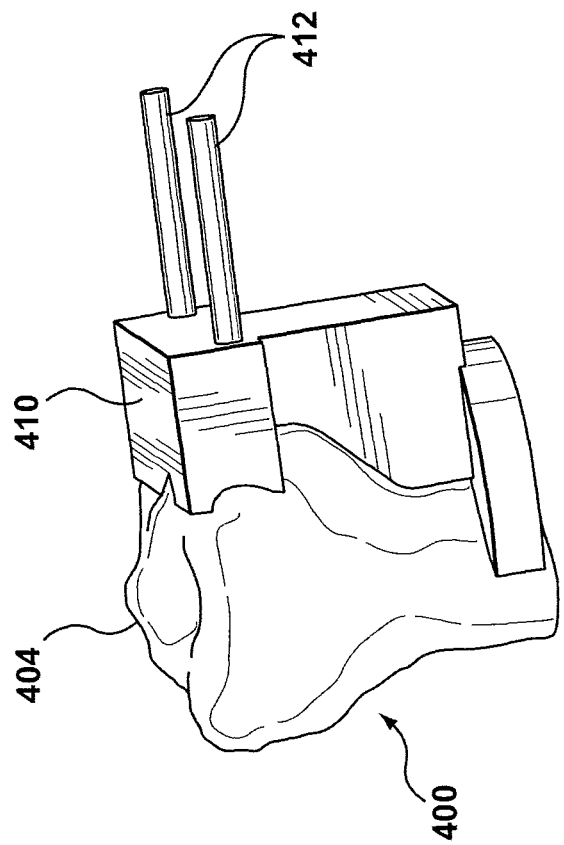
FIGS. 17a and 17b are illustrations of how a guidance tool can similarly be used in total knee arthroplasty.
Figure 17A:
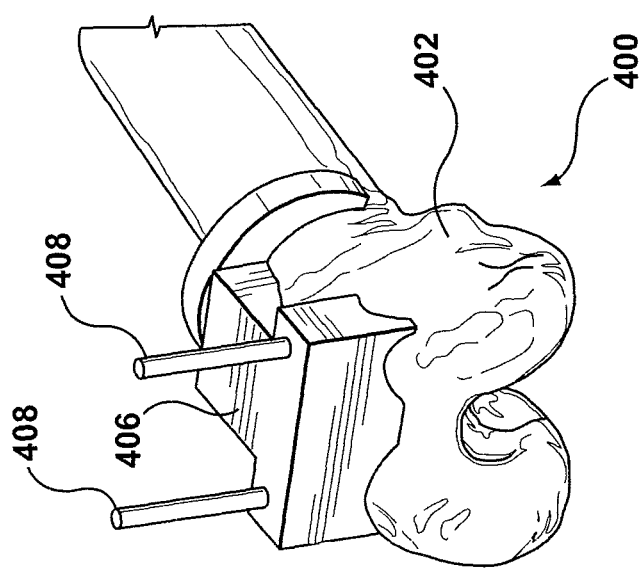

FIGS. 17a and 17b provide a further embodiment in which the preoperative procedure/methodology and resultant guidance tool are used in total knee arthroplasty. In total knee arthroplasty, a 3-D iso-surface model 400 of the femur 402 and tibia 404 is created and the femoral distal and tibial resection is planned. A patient-specific guidance tool 406 for the femur 402 is created (FIG. 17a), which contains guide mechanisms for guided placement of two guidance pins 408. During the surgery the guidance tool 406 is placed upon the patient's anatomy, positionally verified using a verification tool and pins 408 are then placed into the femur 402. After removing the guidance tool 406 the pins 408 are used to guide a resection block with respect to the preoperative planning of the resection plane. A similar guidance tool 410 is created for the tibia 404 (FIG. 17b), which contains the guide mechanism for guided placement of the pins 412. During surgery these guidance pins 412 allow placement of a resection block with respect to the planned tibial resection plane. As required, the guide mechanisms are adjusted in accordance with any correction required as indicated using the verification tool.

FIGS. 18a and 18b provide further embodiments in which the preoperative procedure/methodology and resultant guidance tool are used in total ankle arthroplasty. Total ankle arthroplasty has, in the past few years, become an accepted method in the treatment of end-stage ankle arthritis. Studies analyzing the long-term outcome of total ankle arthroplasty have shown that initial implant alignment is a very important factor in avoiding intaoperative and post-operative complications. The literature around total ankle arthroplasty has shown a steep learning curve with adoption of this procedure. In particular, obtaining correct alignment of the talar component is problematic since the surgical exposure allows visualization of only a small portion of the talus. This limited view, among other problems, makes it difficult to intraoperatively determine correct position of the initial surgical jig. Highlighting the need for proper component alignment in lower limb arthroplasty is the body of research showing that malalignment and instability are the two most important causes of early (i.e., less than five years) failure in total ankle arthroplasty.

In accordance with the preoperative procedure/methodology described above for hip-resurfacing, the patient is first subjected to preoperative planning in which a CT scan (or other suitable medical imaging) is performed on the affected anatomy. As shown in FIG. 18a, 3-D virtual model 500 is produced from the medical imaging.

During pre-operative planning, the position, size and orientation of the prosthesis components 502a, 502b are determined, as shown in FIG. 18b. The virtual bone models 500 are then loaded, anatomical axes are defined and virtual prosthesis components 502a, 502b are superimposed to the tibia and talus virtual models. At this stage, the user is able to modify the position and orientation of each virtual prosthesis model. The characteristics of the final components are then saved.

Based on preoperative planning, the guidance tool 504 can then be created using the rapid prototype technique, the guidance tool 504 providing the mating surface 506 complementary to the distal tibia and talus 508, which are accessible via the chosen surgical approach.

Figure 18D:
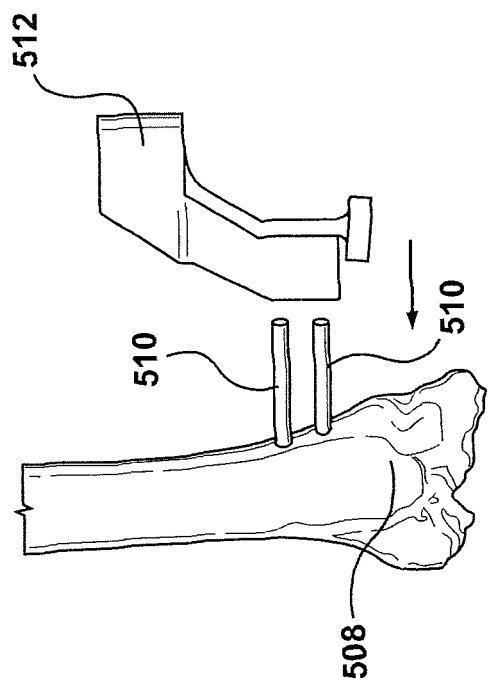
Figure 18C:
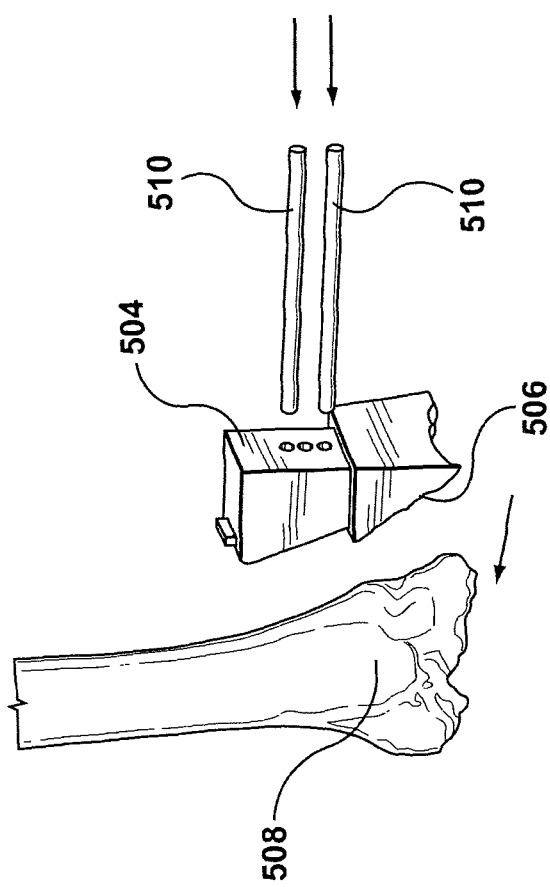

Intraoperatively, the total ankle arthroplasty begins with a conventional surgical approach. After the distal tibia and talus 508 are exposed, as shown in FIG. 18c, the guidance 506 tool is fitted to the corresponding registration surface of the patient's anatomy, drill sleeves are inserted, or adjusted with realignment sleeves if necessary, and the guide pins 510 are drilled into position. With the guidance tool removed, as shown in FIG. 18d, a conventional planar tibia resection block 512 can be fitted to the tibia 508. Resection can then be performed. Position of the cutting guide may be confirmed fluoroscopically prior to cutting the bone.

While exemplified largely within the framework of drilling and pin placement, the preoperative process described above may find application in the development of other guidance tools suited for use with other medical instruments. Guidance tools may be preoperatively planned and manufactured that are suitable for guiding instruments intended for cutting, reaming and resurfacing. Shown in FIGS. 19a through 19c is an alternate procedure and guidance tool 600 for Total Ankle Arthroplasty in which the guide mechanism comprises a guidance block 602 used to guide a saw blade, instead of setting guide pins as shown in FIG. 18c. In such a procedure, the preoperative planning of the guidance tool 600 is similar to that discussed above, except that the preoperatively defined trajectory is identified as a plane upon which the saw is to be directed. When being used intraoperatively, the guidance tool 600 is fitted to the patient's anatomy, and verified for accurate placement. Once positionally verified, the guide mechanism is fitted with an appropriate guide block 602 comprising a slot 604 for fitting a saw blade 606. The slot 604 is dimensioned to fit the blade, and direct the blade along the preoperatively determined trajectory plane. Should adjustments be necessary based on measurements taken by the verification tool, alternate realignment guide blocks 608 may be used, as shown in FIGS. 19*b* (translational offset) and 19*c* (angular offset).

While shown as a slot in a guide block, the guidance tool may provide a bearing surface on one or more edges to guide a saw blade or similar implement (e.g., a chisel). A guidance tool may also comprise any combination of guide mechanisms to guide a range of medical instruments. For example, a guidance tool may comprise guide mechanisms for setting a plurality of pins, while also providing a guide mechanism suited for receipt of a guide block dimensioned to guide a saw blade.

The embodiment of the procedure described above enables the intraoperative use of individualized patient-specific templates or guidance tools to increase overall accuracy and success during bone and joint surgery. As described, the patient-specific guidance tool is created from a pre-operative survey of the anatomy of the patient. The pre-operative steps of surveying and modeling the anatomy provide a plan for central pin alignment based on precision values used during intraoperative navigation. Furthermore the preoperative planning provides a mathematical quality value for registration (figure of merit), using the individual patient-specific guidance tool. The value reflects the ability to fit the guidance tool exactly to one position, specific to the patient being treated. In addition, in the event a misalignment is identified intraoperatively, offset drill sleeves can be used to correct the noted misalignment, so as to achieve the preoperatively defined pin trajectory. In fact, 3-D trajectory analysis on 25 hip-resurfacing procedures using the antero-lateral approach has shown a high degree of trajectory accuracy. The average deviation of the navigated valgus angle compared to the planned angle was determined to be 1.46° varus, with a standard deviation of 3.57°. No complications such as femoral neck fracture, sepsis, or inflections have been observed.

Figure 20:
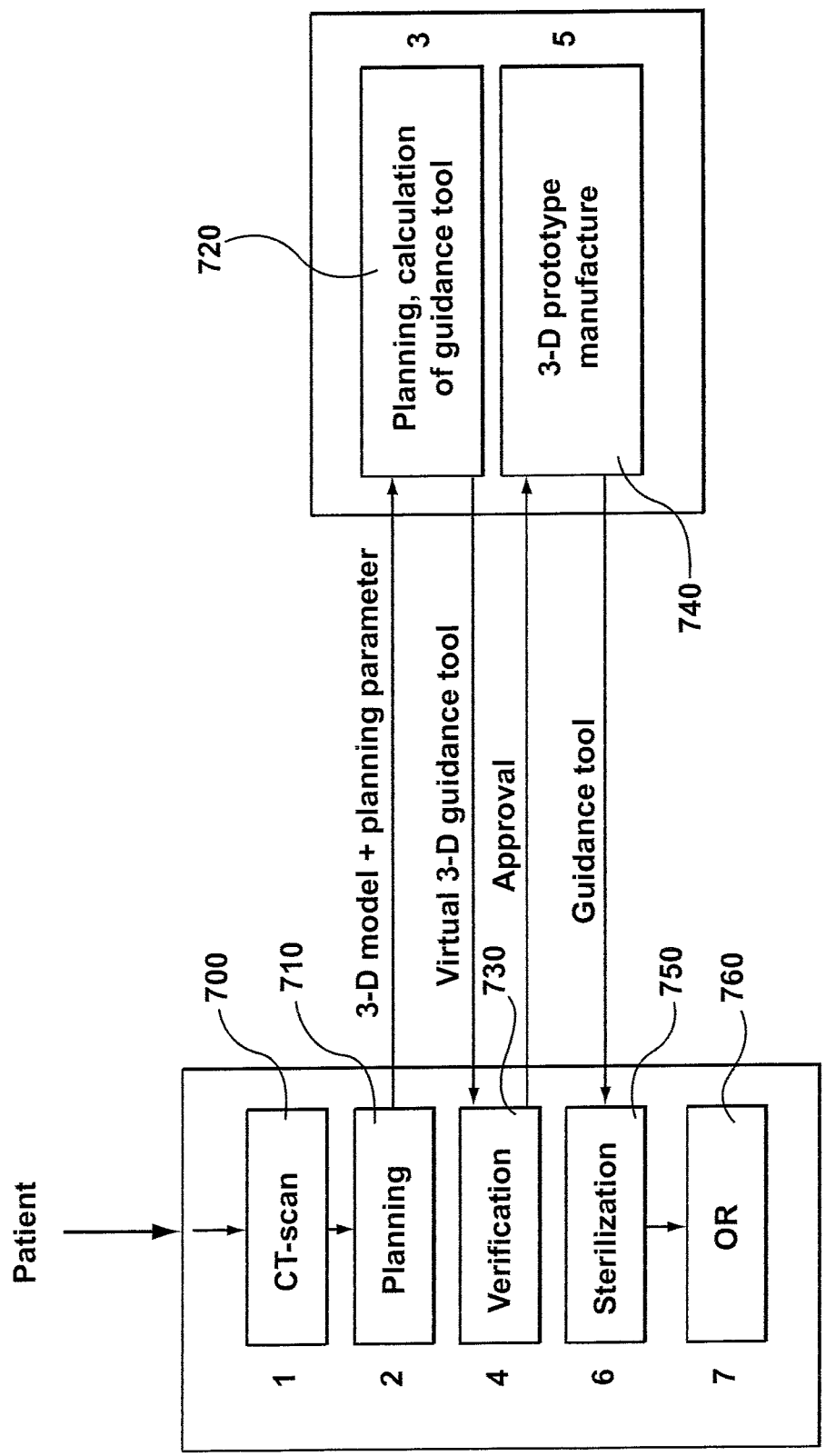
FIG. 20 is a diagram representing the general steps in the preoperative planning stage in which a patient-specific guidance tool is created based on a patient's characteristic anatomy.

In summary the preoperative survey and modelling of the patient's anatomy and the subsequent planning and production of a patient-specific guidance tool will allow clinics without a "computer-assisted engineering team" in-house to achieve the accuracy of computer-assisted surgery. As outlined in FIG. 20, the general steps in the overall procedure are represented as follows:

a. a suitable medical image (e.g., CT scan) of the patient's affected anatomy is obtained and a 3-D model is generated (700);

b. based on the 3-D model of the patient's anatomy, pre-operative planning is conducted to determine the correct placement/trajectories of any manipulations (e.g. pin placement, shaping, etc.) to the anatomy (710);

c. based on the results of preoperative planning, the design of the guidance tool is calculated, taking into consideration factors such as, but not limited to, the specific registration surface of the patient's anatomy (720);

d. the design of the guidance tool undergoes inspection, verification and approval by the requesting user (730);

e. the design is converted into a usable physical form by way of rapid prototype manufacture, and sent to the requesting user (740);

f. the guidance tool is sterilized and prepared for use (either prior to or upon receipt by the user) (750);

g. the guidance tool is used intraoperatively (760).

The procedure described above has a number of notable advantages over the prior art. First, the procedure combines the accuracy benefits of CAS with the precision, repeatability, low cost and ease of use benefits associated with surgical alignment tools. By optimizing and customizing the guidance tool for the specific patient being treated, the tool can be made smaller, thereby reducing the size of the incision during surgery. The procedure is easy to conduct and does not require expensive disposables generally associated with intraoperative computer assisted surgery methodologies. The procedure reduces 'line-of-sight' problems associated with opto-electronic computer assisted surgery. That is, in an operating room configured for conventional computer assisted surgery, there is generally a certain amount of interference between the personnel present and the equipment in place. For example, either the surgeons obstruct the "line-of-sight" of the computer-assist equipment, or the computer-assist equipment interferes with the "line-of-sight" of the surgeons. The above noted procedure reduces such "line-of-sight" problems as the quantity of cumbersome equipment in the operating room is reduced. Moreover, no additional surgical exposure is required. The guidance tool is customized, thereby increasing the precision, and decreasing complications and operating room time. The guidance tool is disposable, and inventory management is optimized. The guidance tool also allows for controlled translational and angular intraoperative adjustments for pin placement.

As will be appreciated, for the various alternate applicable procedures, specialized fasteners may be necessary as would be evident to one skilled in the art. In no way are the techniques, tools and methodologies meant to be limited to hip resurfacing, or any of the exemplary embodiments.

It will be appreciated that, although embodiments have been described and illustrated in detail, various modifications and changes may be made. While several embodiments are described above, some of the features described above can be modified, replaced or even omitted. For example, the mating surface for registering the guidance tool on the patient's anatomy may incorporate any number of characteristic landmarks, from one to a plurality of such features. Although the drilling sleeve is described as being a surgical grade metal (e.g., surgical grade stainless steel, titanium, etc.), other suitable materials such as surgically compatible polymers may be used. Although the guidance tool is manufactured from acrylonitrile butadiene styrene (ABS), other suitable polymer materials and metals may be used. Although rapid prototyping is used to create the guidance tool, other methods may be used to form the necessary tool, such as CNC milling or molding technologies. Although the central pin inserted into the femoral head using the guidance tool is provided with a self-tapping threaded configuration, other suitable pin-anchoring alternatives may be employed, as would be evident to one skilled in the art. Although the verification tool is shown with sliding rulers, the verification tool could be configured with a geared calliper-like or other mechanism. Although the guidance tool is generally shown as a unitary structure, the guide block and the body section may be manufactured separately and attached post-production. In addition, it may be feasible to reuse the guide-block portion or the tool while restricting the disposable portion to the customized body section comprising the mating surface. Although the guide block is described as having a locking key for each landmark, multiple landmark locations may correspond to a single locking key, wherein the landmarks lie on the same plane defined by the position of the locking key. One or more locking keys may be intraoperatively adjusted, and the amount of adjustment may be determined by suitable markings or a scale such as a protractor-like scale on the verification tool and/or the guidance tool. Alternatively, the verification tool may be freed from the one or more locking keys and its position adjusted, the amount of adjustment may be determined by suitable markings or a scale such as a protractor-like scale on the verification tool and/or the guidance tool. Although the verification tool and drilling sleeve each separately use the same channel during the described process, the guidance tool, in particular the guide block, may be configured with separate channels or receptacles for receiving each of these components. Still further alternatives and modifications may occur to those skilled in the art. All such alternatives and modifications are believed to be within the scope of the invention and are covered by the claims appended hereto.

The contents of all cited publications are incorporated herein by reference in their entirety.

The invention claimed is:

1. A guidance tool for intraoperative use during tissue, bone or joint manipulation, comprising:
    a body portion, including:
        a patient-specific mating surface that is preoperatively designed to mate with one or more first landmarks of a corresponding registration surface of the patient's anatomy, the mating surface, for positioning the guidance tool on the registration surface of the patient's anatomy; and
        at least one guide mechanism adapted to guide at least one medical instrument at one or more position and trajectory relative to the one or more first landmarks of the patient's anatomy; and
    a verification tool that removably engages the body portion;
    wherein the verification tool comprises a pointer that is adapted to point to one or more preoperatively selected second landmarks on the patient's anatomy, to verify at least one of (i) the position of the body portion on the patient's anatomy and (ii) the position and trajectory of the at least one medical instrument when the at least one medical instrument is inserted into the at least one guide mechanism;
    wherein the one or more first landmarks are different from the one or more second landmarks; and
    wherein the one or more first landmarks and the one or more second landmarks consist of bony structures and/or soft tissue.

2. The guidance tool of claim 1, wherein the body portion further comprises a stability component.

3. The guidance tool of claim 1, wherein the mating surface comprises a profile that is complementary to the one or more first landmarks on the registration surface of the patient's anatomy.

4. The guidance tool of claim 1, wherein the verification tool comprises at least one graduated section for providing misalignment values of the guidance tool relative to one or more preoperatively selected second landmarks on the patient's anatomy.

5. The guidance tool of claim 1, wherein the verification tool comprises two graduated sections, a first graduated section providing misalignment values in a longitudinal direction, and a second graduated section providing misalignment values in a radial direction.

6. The guidance tool of claim 1, further comprising locking keys on the body portion for aligning the verification tool in a preoperatively defined position relative to one or more preoperatively selected second anatomical landmarks.

7. The guidance tool of claim 1, wherein the guide mechanism comprises a guide channel and corresponding instrument sleeve adapted for placement within, the guide channel and for guiding the medical instrument at one or more position and trajectory relative to the patient's anatomy.

8. The guidance tool of claim 1, wherein the at least one guide mechanism is adjustable to alter the one or more position, trajectory, or position and trajectory of the at least one medical instrument during intraoperative use.

9. The guidance tool of claim 8, wherein the guide mechanism comprises a guide channel and corresponding realignment sleeve adapted for placement within the guide channel and for guiding the medical instrument, the realignment sleeve providing a realignment of the medical instrument position and/or trajectory.

10. The guidance tool of claim 9, wherein the realignment sleeve is configured with:
    an offset at a selected distance relative to a central axis of the sleeve;
    an offset at a selected angle relative to a central axis of the sleeve; or
    a combined offset at a selected distance and a selected angle relative to a central axis of the sleeve.

11. A method of using a guidance tool intraoperatively during tissue, bone or joint manipulation, comprising:
    placing a preoperatively designed patient-specific mating surface of a body portion of the guidance tool on a patient's anatomy, so that that the mating surface mates with one or more first landmarks of a corresponding registration surface of the patient's anatomy;
    wherein the mating surface is for positioning the guidance tool on the registration surface of the patient's anatomy; and
    wherein the body portion comprises at least one guide mechanism adapted to guide at least one medical instrument at one or more position and trajectory relative to the one or more first landmarks of the patient's anatomy; and
    using a verification tool that removably engages the body portion to point to one or more preoperatively selected second landmarks on the patient's anatomy, to verify at least one of (i) the position of the body portion on the patient's anatomy and (ii) the position and trajectory of the at least one medical instrument when the at least one medical instrument is inserted into the at least one guide mechanism;
    wherein the one or more first landmarks are different from the one or more second landmarks; and
    wherein the one or more first landmarks and the one or more second landmarks consist of bony structures and/or soft tissue.

12. The method of claim 11, comprising using a graduated section of the verification tool to provide misalignment values of the guidance tool relative to one or more preoperatively selected second landmarks on the patient's anatomy.

13. The method of claim 11, comprising using two graduated sections of the verification tool, wherein a first graduated section provides misalignment values in a longitudinal direction, and a second graduated section provides misalignment values in a radial direction.

14. The method of claim 11, further comprising using locking keys on the body portion to align the verification tool in a preoperatively defined position relative to one or more preoperatively selected second anatomical landmarks.

15. The method of claim 11, further comprising inserting an instrument sleeve into the guide channel to guide the at least one medical instrument at one or more position and trajectory relative to the patient's anatomy.

16. The method of claim 11, further comprising inserting a realignment sleeve into the guide channel to guide the at least one medical instrument and provide a realignment of the at least one medical instrument position and/or trajectory.

17. The method of claim 16, comprising providing the realignment with:
   an offset at a selected distance relative to a central axis of the sleeve;
   an offset at a selected angle relative to a central axis of the sleeve; or
   a combined offset at a selected distance and a selected angle relative to a central axis of the sleeve.

* * * * *